US007875688B2

(12) United States Patent
Dershem et al.

(10) Patent No.: US 7,875,688 B2
(45) Date of Patent: *Jan. 25, 2011

(54) FREE-RADICAL CURABLE POLYESTERS AND METHODS FOR USE THEREOF

(75) Inventors: Stephen M. Dershem, San Diego, CA (US); Farhad G. Mizori, La Mesa, CA (US)

(73) Assignee: Designer Molecules, Inc., San Diego, CA (US)

( * ) Notice: Subject to any disclaimer, the term of this patent is extended or adjusted under 35 U.S.C. 154(b) by 305 days.

This patent is subject to a terminal disclaimer.

(21) Appl. No.: 11/974,673

(22) Filed: Oct. 15, 2007

(65) Prior Publication Data

US 2008/0210375 A1 Sep. 4, 2008

Related U.S. Application Data

(63) Continuation-in-part of application No. 11/145,382, filed on Jun. 3, 2005, now Pat. No. 7,285,613.

(60) Provisional application No. 60/577,004, filed on Jun. 4, 2004, provisional application No. 60/655,709, filed on Feb. 23, 2005.

(51) Int. Cl.
*C08F 4/80* (2006.01)
*C07C 69/76* (2006.01)
*C07C 69/74* (2006.01)

(52) U.S. Cl. .................. 526/285; 526/319; 526/346; 526/313; 560/90; 560/121; 560/122; 560/127

(58) Field of Classification Search ............... 526/285, 526/319, 313, 346; 560/90, 121, 122, 127
See application file for complete search history.

(56) References Cited

U.S. PATENT DOCUMENTS

| | | | |
|---|---|---|---|
| 3,336,266 A | 8/1967 | McConnell et al. | |
| 3,379,041 A * | 4/1968 | Schmid et al. | 70/456 R |
| 3,739,041 A | 6/1973 | Schmid et al. | |
| 3,918,393 A | 11/1975 | Hahn | |
| 4,363,907 A | 12/1982 | Hefner et al. | |
| 4,395,462 A | 7/1983 | Polmanteer | |
| 4,483,898 A | 11/1984 | Schonhorn et al. | |
| 4,540,829 A | 9/1985 | Hefner, Jr. | |
| 4,560,768 A | 12/1985 | Hefner et al. | |
| 4,623,696 A | 11/1986 | Mabrey et al. | |
| 4,753,982 A | 6/1988 | Hefner, Jr. | |
| 4,774,267 A | 9/1988 | Weintraub | |
| 4,777,209 A | 10/1988 | Hefner, Jr. | |
| 4,968,738 A | 11/1990 | Dershem | |
| 5,045,127 A | 9/1991 | Dershem et al. | |
| 5,064,480 A | 11/1991 | Dershem et al. | |
| 5,128,746 A | 7/1992 | Pennisi et al. | |
| 5,155,177 A | 10/1992 | Frihart | |
| 5,232,962 A | 8/1993 | Dershem et al. | |
| 5,306,333 A | 4/1994 | Dershem et al. | |
| 5,358,992 A | 10/1994 | Dershem et al. | |
| 5,376,721 A | 12/1994 | McGarry et al. | |
| 5,403,389 A | 4/1995 | Dershem | |
| 5,428,105 A | 6/1995 | McGarry et al. | |
| 5,430,112 A | 7/1995 | Sakata et al. | |
| 5,437,964 A | 8/1995 | Lapin et al. | |
| 5,447,988 A | 9/1995 | Dershem et al. | |
| 5,489,641 A | 2/1996 | Dershem | |
| 5,567,761 A | 10/1996 | Song | |
| 5,596,669 A | 1/1997 | Murphy et al. | |
| 5,646,241 A | 7/1997 | Dershem et al. | |
| 5,707,782 A | 1/1998 | Economy et al. | |
| 5,714,086 A | 2/1998 | Osuna et al. | |
| 5,717,034 A | 2/1998 | Dershem et al. | |
| 5,718,941 A | 2/1998 | Dershem et al. | |
| 5,753,748 A | 5/1998 | Dershem et al. | |
| 5,861,111 A | 1/1999 | Dershem et al. | |
| 5,880,170 A | 3/1999 | Imura et al. | |
| 5,891,566 A | 4/1999 | Sakumoto et al. | |
| 5,969,036 A | 10/1999 | Dershem | |
| 5,973,166 A | 10/1999 | Mizori et al. | |
| 6,034,194 A | 3/2000 | Dershem et al. | |
| 6,034,195 A | 3/2000 | Dershem et al. | |
| 6,063,828 A | 5/2000 | Ma et al. | |
| 6,121,358 A | 9/2000 | Dershem et al. | |
| 6,187,886 B1 | 2/2001 | Husson, Jr. et al. | |
| 6,211,320 B1 | 4/2001 | Dershem et al. | |

(Continued)

FOREIGN PATENT DOCUMENTS

| | | |
|---|---|---|
| EP | 1834969 | 9/2007 |
| JP | 57036125 | 2/1982 |
| JP | 2003002919 | 1/2003 |
| JP | 2003002919 A * | 1/2003 |
| JP | 2004037475 | 2/2004 |
| JP | 2004037475 A | 5/2004 |

(Continued)

OTHER PUBLICATIONS

International Search Report for Related PCT Application No. PCT/US2005/019369, Mar. 16, 2006.
"International Search Report for PCT Application No. PCT/US06/07943" Sep. 25, 2006, p. 1-2.
"Supplementary Search Report for EP application 05757391.7" Mar. 13, 2009, p. 1-3.
DSM, "Hybrane (TM) DSM's new dendritic polymers", DSM New Business Development *product literature 99-1c* 1999, 1-10.
Klang, "Radiation-curable Hyperbranched Polyester Acrylates", PCI Magazine Apr. 2007, 98-101.

*Primary Examiner*—Michael M Bernshteyn
(74) *Attorney, Agent, or Firm*—The Law Office of Jane K. Babin, Professional Corporation; Jane K. Babin

(57) ABSTRACT

The invention is based on the discovery that certain polyester compounds bearing are useful as b-stageable and/or liquid adhesives for the microelectronic packaging industry.

19 Claims, No Drawings

U.S. PATENT DOCUMENTS

| | | |
|---|---|---|
| 6,265,530 B1 | 7/2001 | Herr et al. |
| 6,281,314 B1 | 8/2001 | Tong et al. |
| 6,313,189 B1 | 11/2001 | Wenz et al. |
| 6,316,566 B1 | 11/2001 | Ma et al. |
| 6,355,750 B1 | 3/2002 | Herr |
| 6,403,757 B1 * | 6/2002 | Yabuta et al. ............... 528/310 |
| 6,423,780 B1 | 7/2002 | Dersehm et al. |
| 6,429,281 B1 | 8/2002 | Dersehm et al. |
| 6,451,929 B1 | 9/2002 | Smits et al. |
| 6,482,899 B2 * | 11/2002 | Ohashi et al. ............... 525/486 |
| 6,521,731 B2 | 2/2003 | Dersehm et al. |
| 6,577,013 B1 | 6/2003 | Glenn et al. |
| 6,620,946 B2 | 9/2003 | Dersehm et al. |
| 6,699,929 B2 | 3/2004 | Musa et al. |
| 6,743,852 B2 | 6/2004 | Dersehm et al. |
| 6,750,301 B1 | 6/2004 | Bonneau et al. |
| 6,777,027 B2 | 8/2004 | Daly et al. |
| 6,790,597 B2 | 9/2004 | Dersehm et al. |
| 6,825,245 B2 | 11/2004 | Dersehm et al. |
| 6,831,132 B2 | 12/2004 | Liu et al. |
| 6,852,814 B2 | 2/2005 | Dersehm et al. |
| 6,916,856 B2 | 7/2005 | Dersehm et al. |
| 6,946,523 B2 | 9/2005 | Dersehm et al. |
| 6,960,636 B2 | 11/2005 | Dersehm et al. |
| 6,963,001 B2 | 11/2005 | Dersehm et al. |
| 7,102,015 B2 | 9/2006 | Dersehm et al. |
| 7,157,587 B2 | 1/2007 | Mizoir et al. |
| 7,176,044 B2 | 2/2007 | Forray et al. |
| 7,199,249 B2 | 4/2007 | Liu et al. |
| 7,208,566 B2 | 4/2007 | Mizori et al. |
| 7,228,161 B2 | 6/2007 | Chin |
| 7,230,055 B2 | 6/2007 | Musa |
| 7,285,613 B2 | 10/2007 | Dersehm et al. |
| 7,309,724 B2 | 12/2007 | Dersehm et al. |
| 7,517,925 B2 | 4/2009 | Dersehm et al. |
| 7,678,879 B2 | 3/2010 | Dersehm |
| 2002/0002238 A1 | 1/2002 | Laplante et al. |
| 2002/0062923 A1 | 5/2002 | Forray |
| 2002/0099168 A1 | 7/2002 | Dersehm et al. |
| 2002/0188137 A1 | 12/2002 | Dersehm et al. |
| 2002/0193541 A1 | 12/2002 | Dersehm et al. |
| 2002/0198356 A1 | 12/2002 | Dersehm et al. |
| 2003/0008992 A1 | 1/2003 | Dersehm et al. |
| 2003/0055121 A1 | 3/2003 | Dersehm et al. |
| 2003/0060531 A1 | 3/2003 | Dersehm et al. |
| 2003/0083436 A1 | 5/2003 | Deitch |
| 2003/0087999 A1 | 5/2003 | Dersehm et al. |
| 2003/0109666 A1 | 6/2003 | Dersehm et al. |
| 2003/0125551 A1 | 7/2003 | Dersehm et al. |
| 2003/0129438 A1 | 7/2003 | Becker et al. |
| 2003/0166746 A1 | 9/2003 | Zhou et al. |
| 2003/0178138 A1 | 9/2003 | Taukagoshi |
| 2003/0199638 A1 | 10/2003 | Liu et al. |
| 2003/0208016 A1 | 11/2003 | Dersehm et al. |
| 2004/0006166 A1 | 1/2004 | Liu et al. |
| 2004/0019224 A1 | 1/2004 | Dersehm et al. |
| 2004/0067606 A1 | 4/2004 | Fehr et al. |
| 2004/0068027 A1 | 4/2004 | Daly et al. |
| 2004/0077798 A1 | 4/2004 | Dershem et al. |
| 2004/0082724 A1 | 4/2004 | Dershem et al. |
| 2004/0102566 A1 | 5/2004 | Forray et al. |
| 2004/0110859 A1 | 6/2004 | Biro et al. |
| 2004/0122168 A1 | 6/2004 | Murray |
| 2004/0123948 A1 | 7/2004 | Dershem et al. |
| 2004/0225026 A1 | 11/2004 | Mizori et al. |
| 2004/0225045 A1 | 11/2004 | Forray |
| 2004/0225059 A1 | 11/2004 | Mizori et al. |
| 2005/0027082 A1 | 2/2005 | Narayan-Sarathy et al. |
| 2005/0107542 A1 | 5/2005 | Liu et al. |
| 2005/0136620 A1 | 6/2005 | Dershem et al. |
| 2005/0137277 A1 | 6/2005 | Dershem et al. |
| 2005/0267254 A1 | 12/2005 | Mizori et al. |
| 2005/0272888 A1 | 12/2005 | Dershem et al. |
| 2006/0009578 A1 | 1/2006 | Dershem |
| 2006/0063014 A1 | 3/2006 | Forray |
| 2006/0069232 A1 | 3/2006 | Dershem |
| 2006/0089447 A1 | 4/2006 | Robertson et al. |
| 2006/0142517 A1 | 6/2006 | Dershem |
| 2007/0155869 A1 | 7/2007 | Dershem et al. |
| 2007/0205399 A1 | 9/2007 | Mizori |
| 2007/0299154 A1 | 12/2007 | Dershem et al. |
| 2008/0017308 A1 | 1/2008 | Dershem et al. |
| 2008/0075961 A1 | 3/2008 | Mizori |
| 2008/0075963 A1 | 3/2008 | Dershem |
| 2008/0075965 A1 | 3/2008 | Dershem |
| 2008/0103240 A1 | 5/2008 | Dershem |
| 2008/0142158 A1 | 6/2008 | Dershem |
| 2008/0146738 A1 | 6/2008 | Dershem |
| 2008/0160315 A1 | 7/2008 | Forray et al. |
| 2008/0191173 A1 | 8/2008 | Dershem et al. |
| 2008/0210375 A1 | 9/2008 | Dershem et al. |
| 2008/0251935 A1 | 10/2008 | Dersham |
| 2008/0257493 A1 | 10/2008 | Dershem |
| 2008/0262191 A1 | 10/2008 | Mizori |
| 2009/0061244 A1 | 3/2009 | Dershem |
| 2009/0215940 A1 | 8/2009 | Dershem |
| 2009/0288768 A1 | 11/2009 | Dershem |
| 2010/0041803 A1 | 2/2010 | Dershem |
| 2010/0041823 A1 | 2/2010 | Dershem |
| 2010/0041832 A1 | 2/2010 | Dershem |
| 2010/0041845 A1 | 2/2010 | Dershem et al. |
| 2010/0056671 A1 | 3/2010 | Dershem |
| 2010/0063184 A1 | 3/2010 | Dershem |

FOREIGN PATENT DOCUMENTS

| | | |
|---|---|---|
| WO | WO-8604073 | 7/1986 |
| WO | WO-9406862 | 3/1994 |
| WO | WO-2004060330 | 7/2004 |
| WO | 2004/099331 | 11/2004 |
| WO | WO-2005003231 | 1/2005 |
| WO | WO-2005121190 | 12/2005 |
| WO | WO-2007100329 | 9/2007 |
| WO | WO-2008077141 | 6/2008 |
| WO | WO-2008124797 | 10/2008 |
| WO | WO-2008130894 | 10/2008 |
| WO | WO-2010019832 | 2/2010 |

* cited by examiner

FREE-RADICAL CURABLE POLYESTERS AND METHODS FOR USE THEREOF

RELATED APPLICATIONS

This application is a continuation-in-part of U.S. application Ser. No. 11/145,382, filed Jun. 3, 2005, now U.S. Pat. No. 7,285,613 which in turn claims the benefit of priority of U.S. Provisional Application Ser. No. 60/577,004 filed Jun. 4, 2004, and U.S. Provisional Application Ser. No. 60/655,709 filed Feb. 23, 2005, the entire disclosures of which are incorporated herein by reference.

FIELD OF THE INVENTION

The present invention relates to thermosetting adhesive compositions, methods of preparation and uses therefor. In particular, the present invention relates to thermosetting compounds and compositions containing free radical curable polyester compounds.

BACKGROUND OF THE INVENTION

Adhesive compositions are used for a variety of purposes in the fabrication and assembly of semiconductor packages and microelectronic devices. The more prominent uses include bonding of electronic elements such as integrated circuit chips to lead frames or other substrates, and bonding of circuit packages or assemblies to printed wire boards. Adhesives useful for electronic packaging applications typically exhibit properties such as good mechanical strength, curing properties that do not affect the component or the carrier, and thixotropic properties compatible with application to microelectronic and semiconductor components.

Recently, there has been an increased interest in b-stageable adhesives. A b-stageable material is actually a thermosetting material that has a first solid phase followed by a rubbery stage at elevated temperature, followed by yet another solid phase at an even higher temperature. The transition from the rubbery stage to the second solid phase is known as thermosetting. However, prior to that, the material behaves similarly to a thermoplastic material. Thus, such a material would permit low lamination temperatures while providing high thermal stability. In addition, b-stageable adhesives eliminate many of the storage, handling, dispensing, and processing issues that exist when dispensing an adhesive in a flowable form. Accordingly, there is a continuing need for b-stageable adhesives in the electronic packaging industry.

SUMMARY OF THE INVENTION

The invention is based on the discovery that certain polyester compounds are useful as adhesives for the microelectronic packaging industry. In certain embodiments, the adhesives described herein are b-stageable adhesives. In one embodiment of the invention there are provided compounds having the structure I:

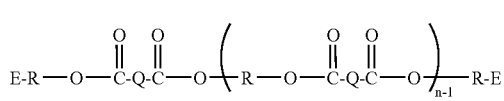

wherein:
R and Q are each independently substituted or unsubstituted aliphatic, aryl, or heteroaryl;
each E is independently acrylate, methacrylate, maleimide, styrenic, vinyl ester, olefin, allyl, vinyl ether, itaconate, fumarate, epoxy, oxetane, oxazoline, benzoxazine, cyanate ester, or propargyl ether; and
n is 1 to about 10.

In another embodiment, there are provided compounds having the structure

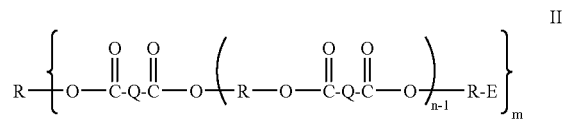

wherein:
R and Q are each independently substituted or unsubstituted aliphatic, aryl, or heteroaryl;
m is 3 or 4;
n is 1 to about 10; and
each E is independently acrylate, methacrylate, maleimide, styrenic, vinyl ester, olefin, allyl, vinyl ether, itaconate, fumarate, epoxy, oxetane, oxazoline, benzoxazine, cyanate ester, or propargyl ether.

In another embodiment, there are provided adhesive compositions including at least one of the above described compounds, and at least one curing initiator.

In yet another embodiment, there are provided b-stageable die-attach pastes including
a) 0.05 weight percent to about 98 weight percent (wt %) of at least one of the above-described compounds, or combinations thereof, based on total weight of the composition,
b) 0 to about 90 wt % of a conductive filler;
d) 0.1 wt % to about 5 wt % of at least one curing initiator, based on total weight of the composition;
e) 0.1 wt % to about 4 wt %, of at least one coupling agent, based on total weight of the composition.

In another embodiment, there are provided assemblies including a first article permanently adhered to a second article by a cured aliquot of the die-attach pastes according to the invention.

In another embodiment, there are provided methods for adhesively attaching a first article to a second article. Such methods can be performed, for example, by (a) applying an aliquot of the adhesive composition of the invention to the first article, (b) bringing the first and second article into intimate contact to form an assembly wherein the first article and the second article are separated only by the adhesive composition applied in (a), and thereafter, (c) subjecting the assembly to conditions suitable to cure the adhesive composition.

In another embodiment, there are provided methods for adhesively attaching a semiconductor die to a substrate. Such methods can be performed, for example, by (a) applying the die attach paste of the invention to the substrate and/or the microelectronic device, (b) subjecting the substrate and/or the microelectronic device to conditions suitable to form a b-staged the curable film, (c) exposing the b-staged curable film to temperature conditions suitable to melt the film, (d) bringing the substrate and the device into intimate contact to form an assembly wherein the substrate and the device are separated only by the die-attach paste, and (e) subjecting the b-staged curable film to conditions suitable to cure the melted film.

DETAILED DESCRIPTION OF THE INVENTION

It is to be understood that both the foregoing general description and the following detailed description are exemplary and explanatory only and are not restrictive of the invention claimed. As used herein, the use of the singular includes the plural unless specifically stated otherwise. As used herein, "or" means "and/or" unless stated otherwise. Furthermore, use of the term "including" as well as other forms, such as "includes," and "included," is not limiting.

The section headings used herein are for organizational purposes only and are not to be construed as limiting the subject matter described.

Unless specific definitions are provided, the nomenclatures utilized in connection with, and the laboratory procedures and techniques of analytical chemistry, synthetic organic and inorganic chemistry described herein are those known in the art. Standard chemical symbols are used interchangeably with the full names represented by such symbols. Thus, for example, the terms "hydrogen" and "H" are understood to have identical meaning. Standard techniques may be used for chemical syntheses, chemical analyses, and formulation.

As used herein, "aliphatic" refers to any alkyl, alkenyl, or cycloalkyl moiety.

As used herein, "alkyl" refers to straight or branched chain hydrocarbyl groups having from 1 up to about 500 carbon atoms. Whenever it appears herein, a numerical range, such as "1 to 500" or "$C_1$-$C_{500}$", refers to each integer in the given range; e.g., "$C_1$-$C_{500}$ alkyl" means that an alkyl group may comprise only 1 carbon atom, 2 carbon atoms, 3 carbon atoms, etc., up to and including 500 carbon atoms, although the term "alkyl" also includes instances where no numerical range of carbon atoms is designated. "Substituted alkyl" refers to alkyl moieties bearing substituents including alkyl, alkenyl, alkynyl, hydroxy, oxo, alkoxy, mercapto, cycloalkyl, substituted cycloalkyl, heterocyclic, substituted heterocyclic, aryl, substituted aryl, heteroaryl, substituted heteroaryl, aryloxy, substituted aryloxy, halogen, haloalkyl, cyano, nitro, nitrone, amino, amido, —C(O)H, —C(O)O—, —C(O)—, —S—, —S(O)$_2$, —OC(O)—O—, —NR—C(O), —NR—C(O)—NR, —OC(O)—NR, wherein R is H or lower alkyl, acyl, oxyacyl, carboxyl, carbamate, sulfonyl, sulfonamide, sulfuryl, and the like.

As used herein, "cycloalkyl" refers to cyclic ring-containing groups containing in the range of about 5 up to about 20 carbon atoms, and "substituted cycloalkyl" refers to cycloalkyl groups further bearing one or more substituents as set forth above. In some embodiments, the cycloalkyl refers to cyclic ring-containing groups containing in the range of about 5 up to about 12 carbon atoms As used herein, "aryl" refers to aromatic groups having in the range of 6 up to 14 carbon atoms and "substituted aryl" refers to aryl groups further bearing one or more substituents as set forth above.

As used herein, "heterocyclic" refers to cyclic (i.e., ring-containing) groups containing one or more heteroatoms (e.g., N, O, S, or the like) as part of the ring structure, and having in the range of 3 up to 20 carbon atoms and "substituted heterocyclic" refers to heterocyclic groups further bearing one or more substituents as set forth above. The term "heterocyclic" is also intended to refer to heteroaryl moieties.

As used herein, "alkenyl" refers to straight or branched chain hydrocarbyl groups having at least one carbon-carbon double bond, and having in the range of about 2 up to 500 carbon atoms, and "substituted alkenyl" refers to alkenyl groups further bearing one or more substituents as set forth above.

As used herein, the term "acrylate" refers to a compound bearing at least one moiety having the structure:

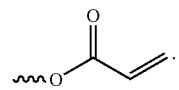

As used herein, the term "methacrylate" refers to a compound bearing at least one moiety having the structure:

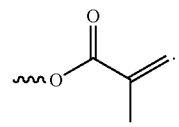

As used herein, the term "maleimide" refers to a compound bearing at least one moiety having the structure:

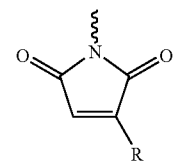

Where R=H, or Me.

As used herein, the term "epoxy" refers to a compound bearing at least one moiety having the structure:

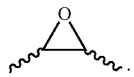

As used herein, the term "vinyl ether" refers to a compound bearing at least one moiety having the structure:

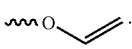

As used herein, the term "acrylamide" refers to a compound bearing at least one moiety having the structure:

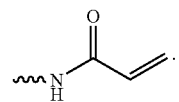

As used herein, the term "methacrylamide" refers to a compound bearing at least one moiety having the structure:

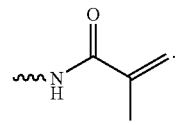

As used herein, "$C_{36}$" refers to a mixture of isomeric $C_{36}$ branched and cyclic hydrocarbon moieties. All of the $C_{36}$ isomers present, for example, in Sovermol 908 are contemplated for use in the practice of the invention.

The invention is based on the discovery that certain polyester compounds are useful as adhesives for the microelectonic packaging industry. In certain embodiments, the adhesives described herein are b-stageable adhesives. In one embodiment of the invention there are provided compounds having the structure I:

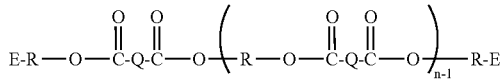

wherein:
R and Q are each independently substituted or unsubstituted aliphatic, aryl, or heteroaryl;
each E is independently acrylate, methacrylate, maleimide, styrenic, vinyl ester, olefin, allyl, vinyl ether, itaconate, fumarate, epoxy, oxetane, oxazoline, benzoxazine, cyanate ester, or propargyl ether; and
n is 1 to about 10.
In another embodiment, there are provided compounds having the structure

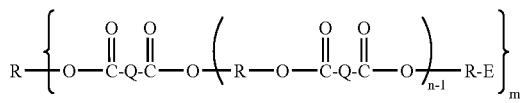

wherein:
R and Q are each independently substituted or unsubstituted aliphatic, aryl, or heteroaryl;
m is 3 or 4;
n is 1 to about 10; and
each E is independently acrylate, methacrylate, maleimide, styrenic, vinyl ester, olefin, allyl, vinyl ether, itaconate, fumarate, epoxy, oxetane, oxazoline, benzoxazine, cyanate ester, or propargyl ether.
In certain embodiments, R is a substituted or unsubstituted cycloalkyl having from 5 to about 20 carbon atoms. In other embodiments, R is a substituted or unsubstituted cycloalkyl having from 5 to about 12 carbon atoms. In some embodiments, R is a substituted or unsubstituted cyclopentyl, cyclohexyl, norbornyl, tetracyclododecyl, or dicyclopentadienyl.
A wide variety of aryl and heteroaryl moieties are contemplated for Q in the practice of the invention. In some embodiments, Q is a substituted or unsubstituted aryl or heteroaryl having from 6 to about 20 carbon atoms. In other embodiments, Q is a substituted or unsubstituted phenyl or naphthyl. In further embodiments, Q is a substituted or unsubstituted cycloalkyl, such as, for example, norbornyl.
In another aspect of this invention it has be discovered that a hybrid of acrylate and methacrylate functional groups offers superior adhesive performance. Acrylates offer faster cure speed and higher thermal stability. Methacrylates are more resistant to hydrolysis and have higher glass transition temperatures. A blend of these two polymerizable functions appears to have better properties than either by itself.

Methacrylate homopolymers are subject to rapid thermal depolymerization at temperatures around 300° C. Incorporation of acrylate residues into the polymethacryate backbone effectively interrupts this depolymerization and boosts the onset for thermal decomposition by about 100° C.

The presence of methacrylate functionality provides an unexpected benefit by reducing the cure speed of acrylate monomers. This moderation of rate of cure appears to be beneficial in terms of residual stress. It has been observed that an all acrylate adhesive generally has lower adhesion than an all methacrylate, or an acrylate-methacrylate blend.

While not wishing to be bound by theory, it is also believed that having acrylate and methacrylate functional groups bound to the same backbone is superior to a physical blend of discreet homo-functional monomers. It is well known that free radical polymerization of dissimilar monomers usually results in a growing polymer chain that preferentially incorporates one specific monomer type much faster than it does another. This property has been characterized for many different mono-functional monomers in terms of "monomer reactivity ratios". The functional polyester monomers described in this invention have been represented by exemplary discrete structures, but they are all, in fact, statistical distributions of molecules. A di-functional polyester acrylate-methacrylate oligomer terminated with a one to one equivalent ratio of acrylate and methacrylate will consist of approximately twenty-five percent each of di-acrylate and di-methacrylate compounds. About fifty percent of the molecules would be terminated by both acrylate and methacrylate residues. This hybridization of functionality at the molecular level is believed to defeat any tendency toward segregation of the thermoset into domains consisting mostly homo-polymers of acrylate or methacrylate functionality. This homogenization of the thermoset architecture is believed to offer improvements in both thermal and hydrolytic resistance.

It should be understood that the benefits of scrambling the thermosetting functional groups is not limited just to combinations of acrylate and methacrylate. Similar benefits can also be achieved where maleimide, vinyl ether, vinyl ester, or styrenic functional groups are incorporated into the monomers. A mixed maleimide-methacrylate terminated polyester, for example, shows a similar benefit in thermal stability as seen in the acrylate-methacrylate combination.

It is understood that a wide variety of polyester compounds are contemplated for use in the practice of the invention. In one embodiment of the invention, the polyester compounds contain acrylate or methacrylate moieties. Some examples of this embodiment are set forth below:

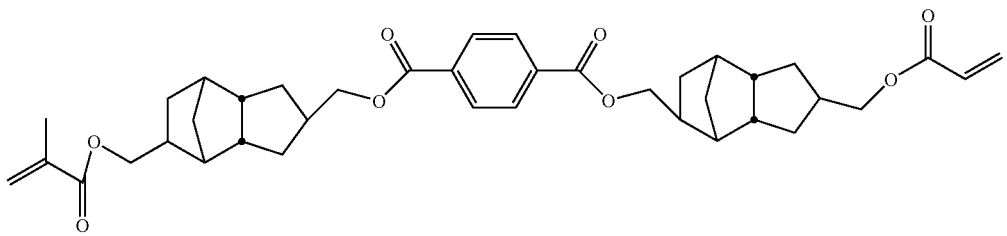

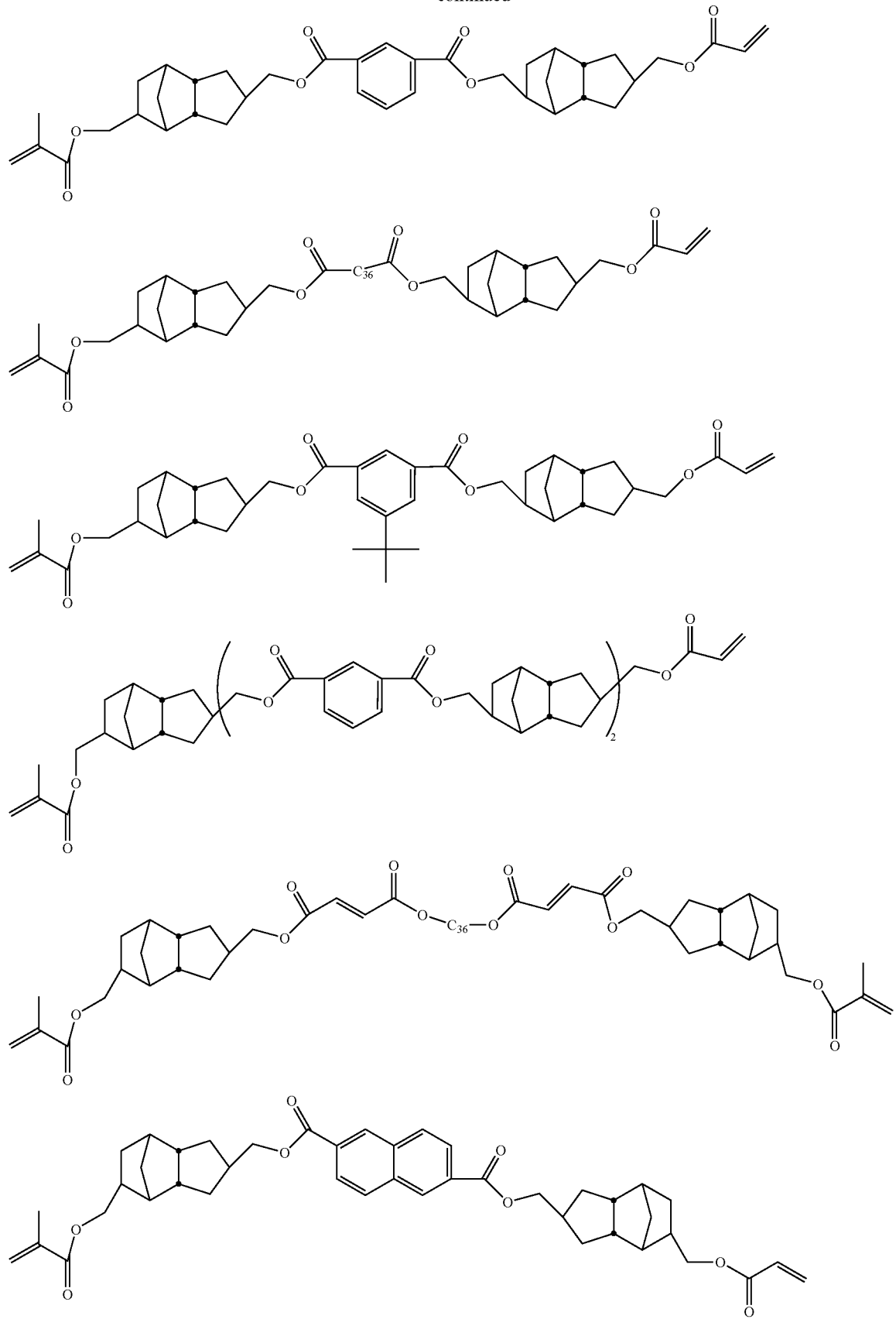

-continued
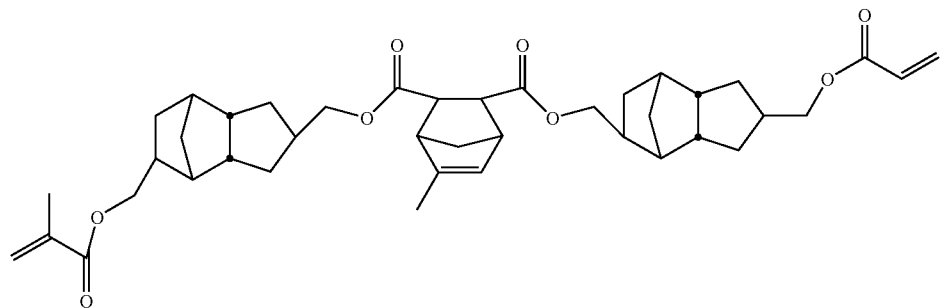
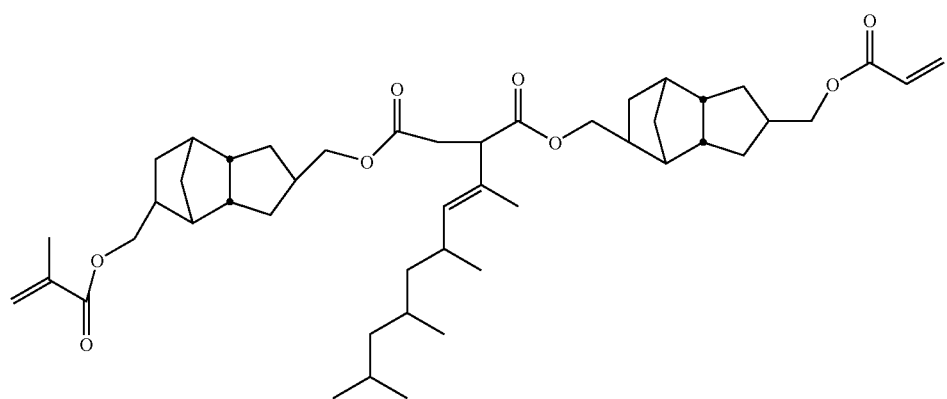
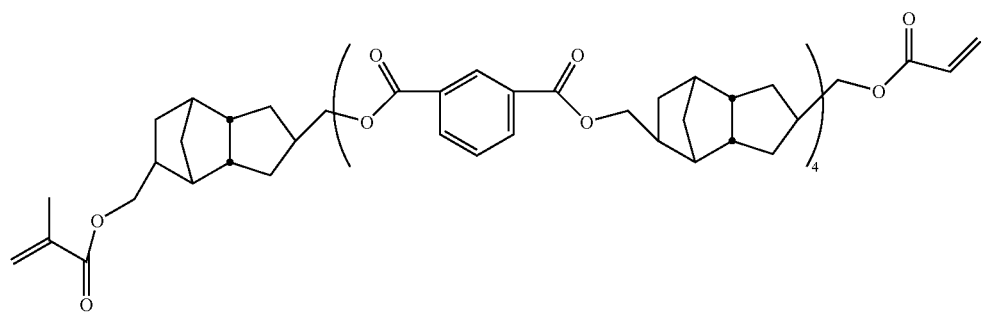
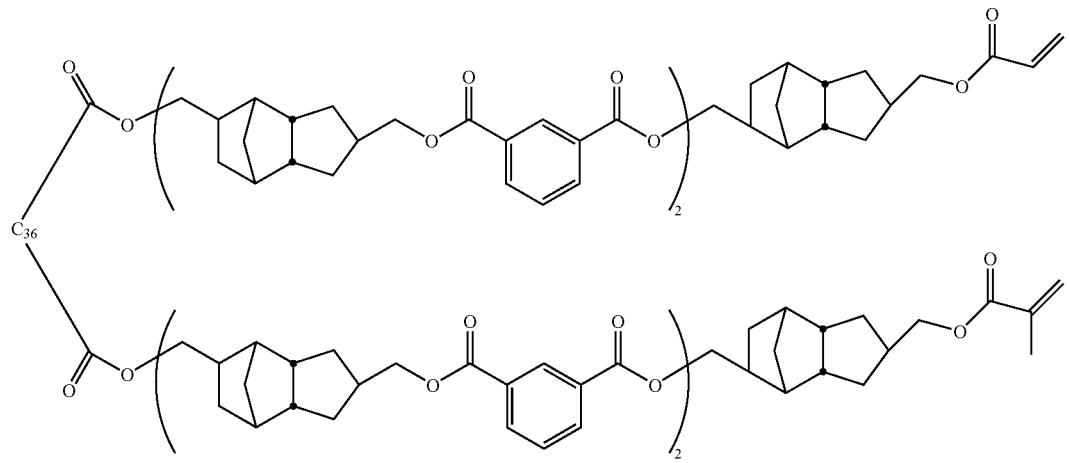

-continued
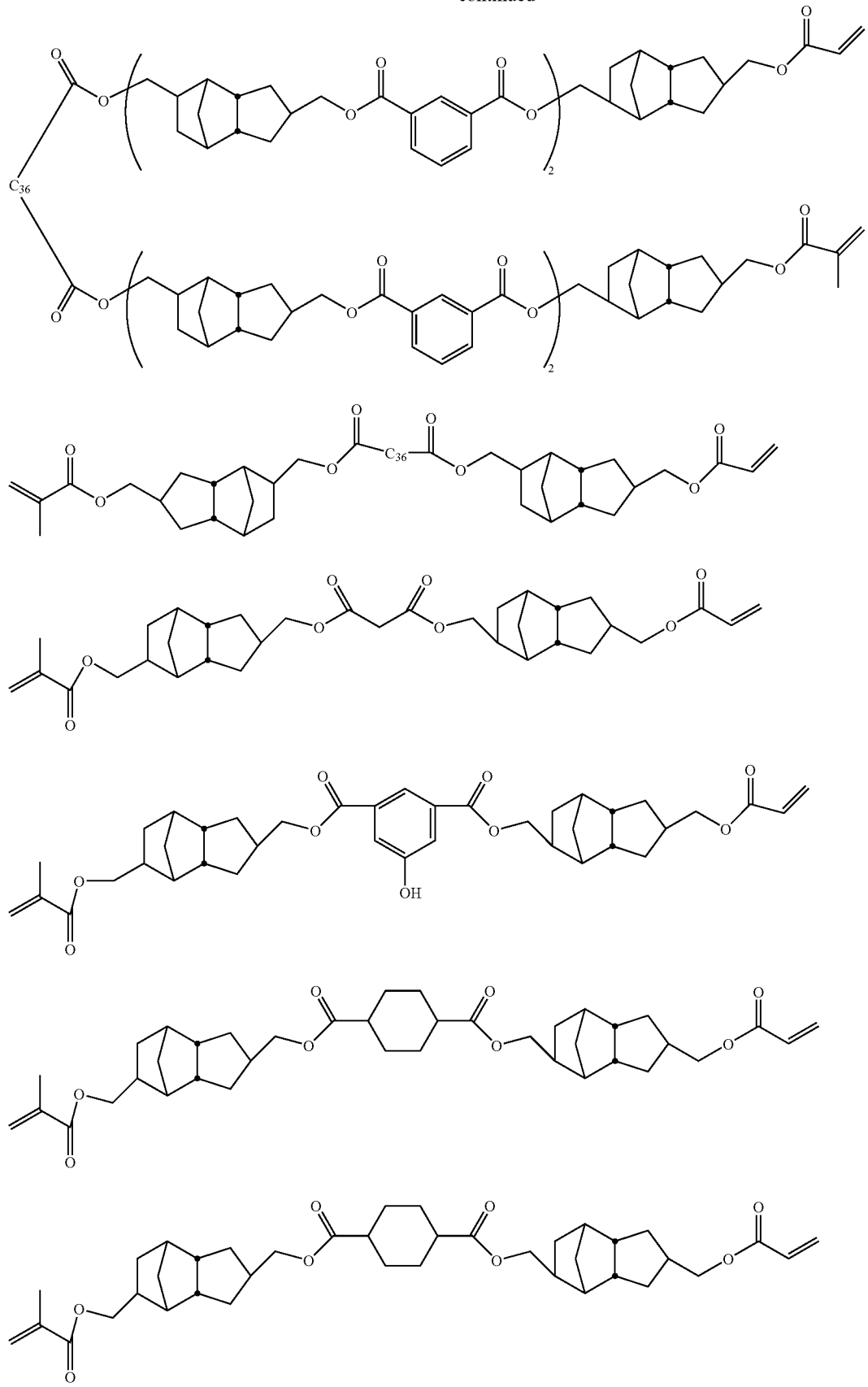

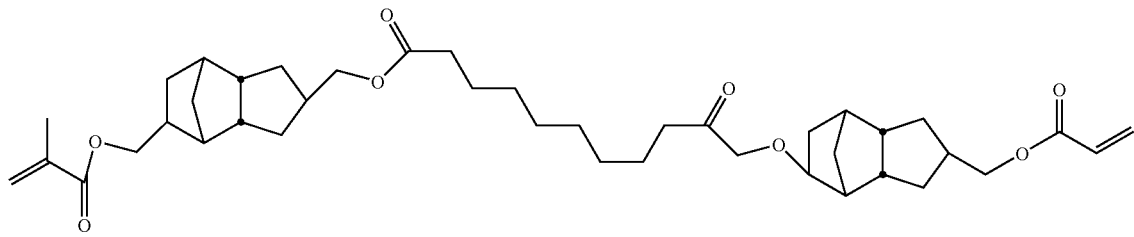
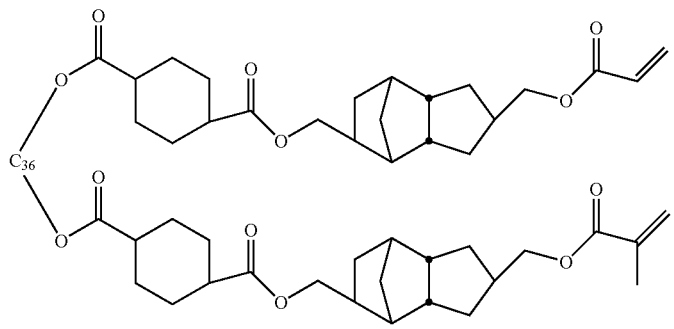
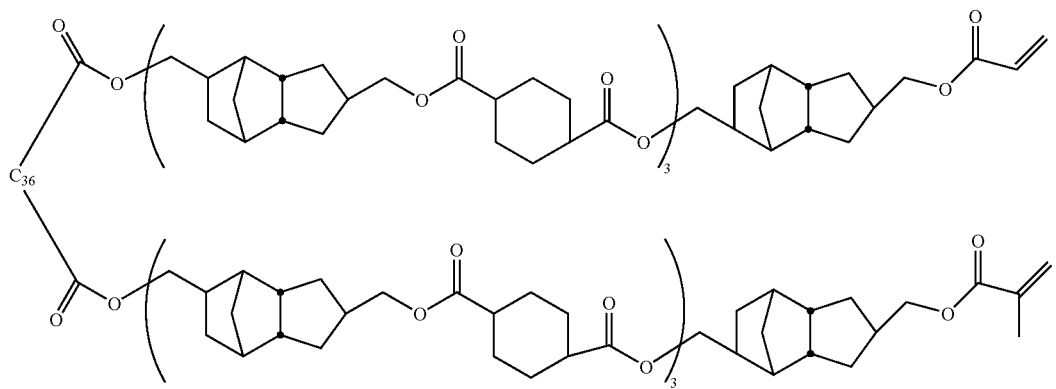
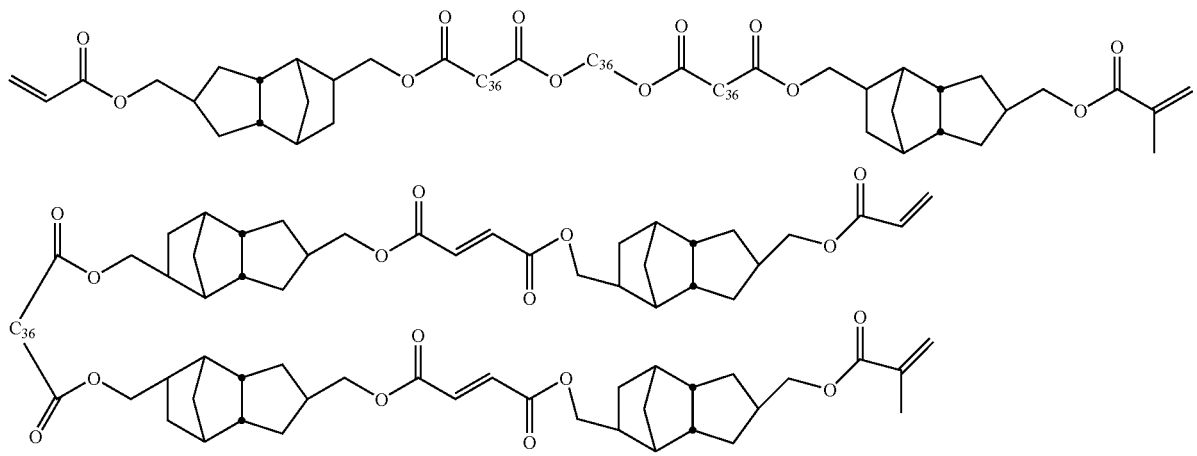

Further exemplary invention compounds include those set forth below:
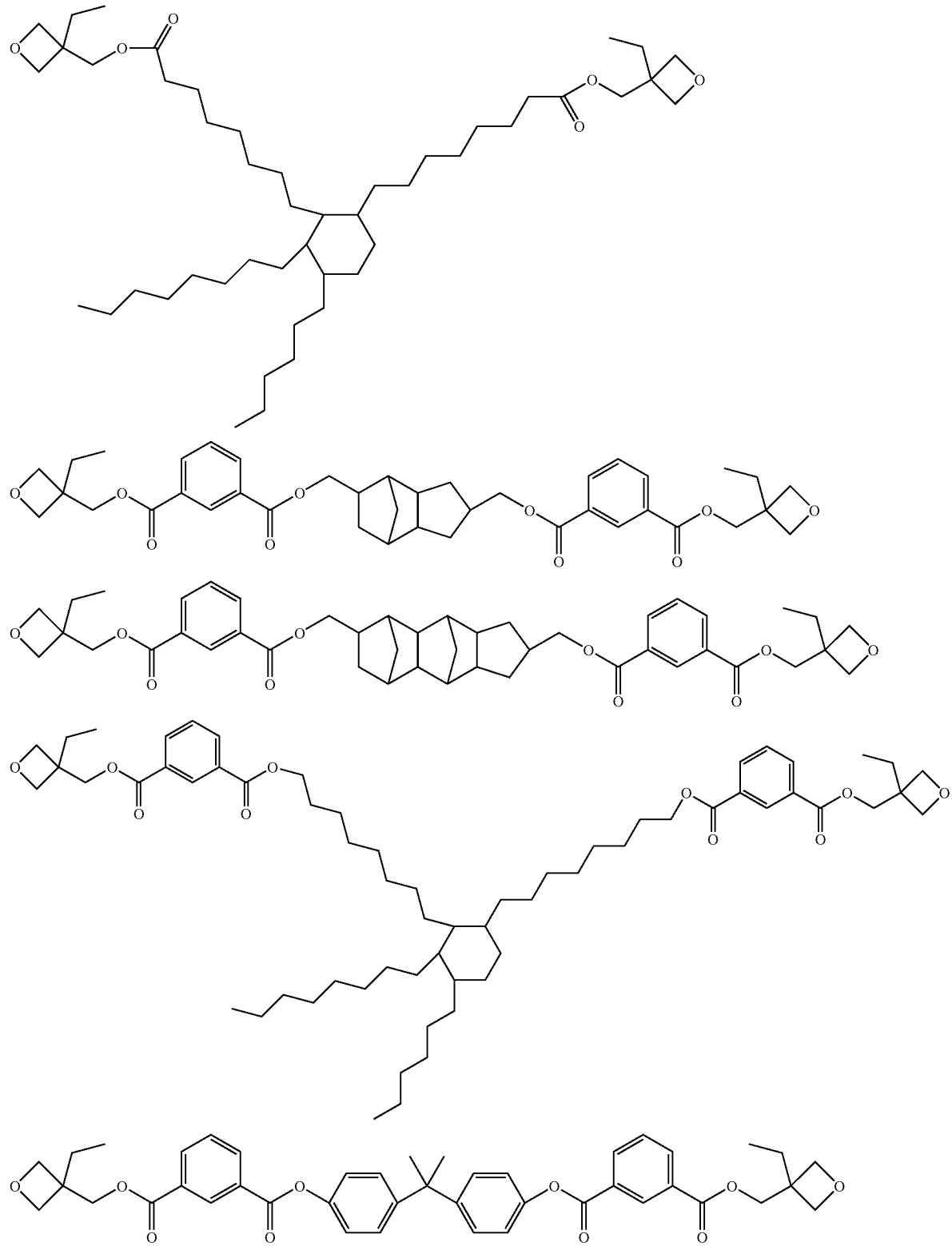

-continued
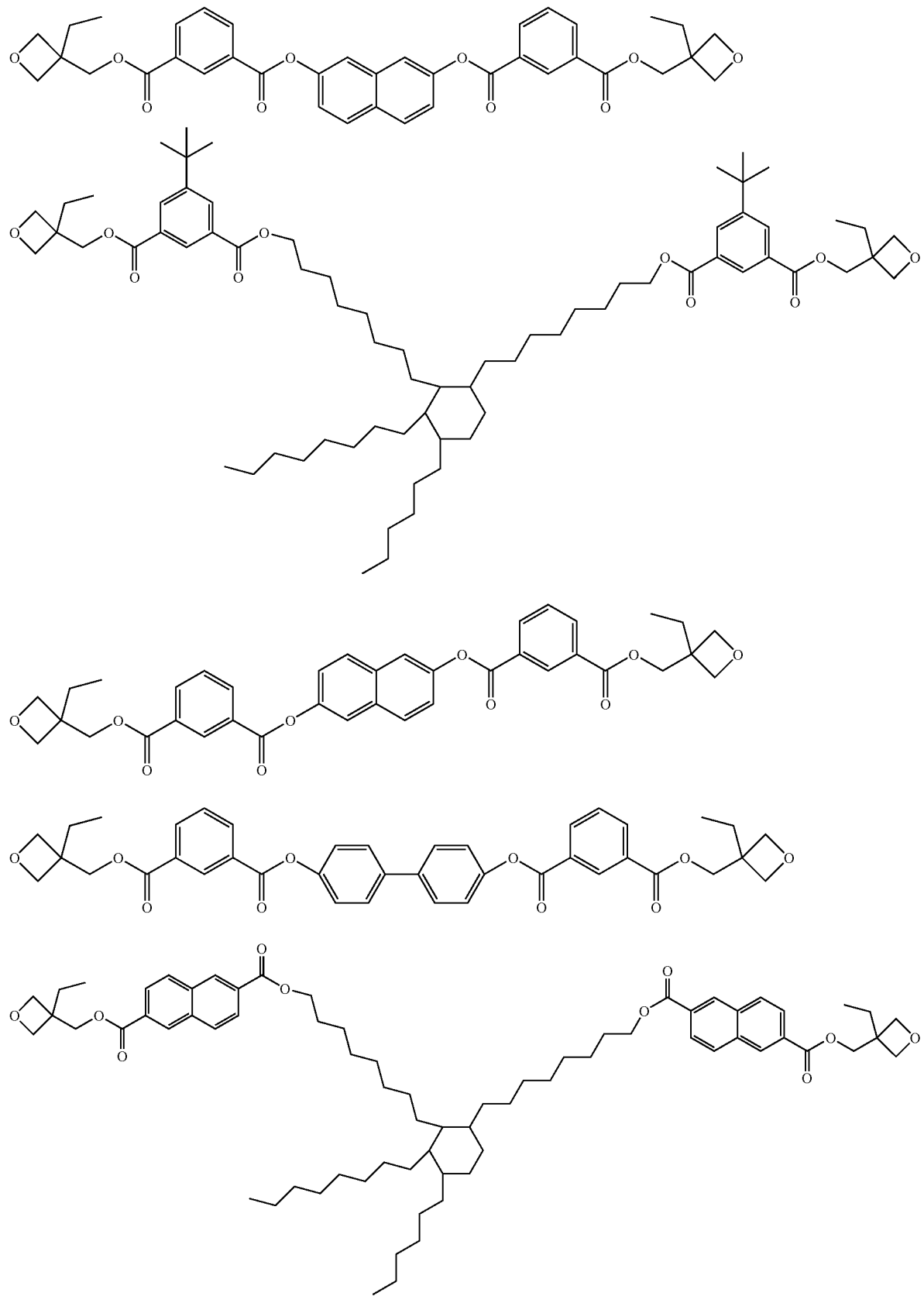

-continued
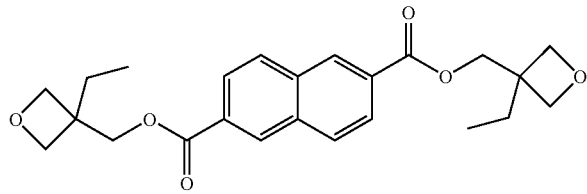
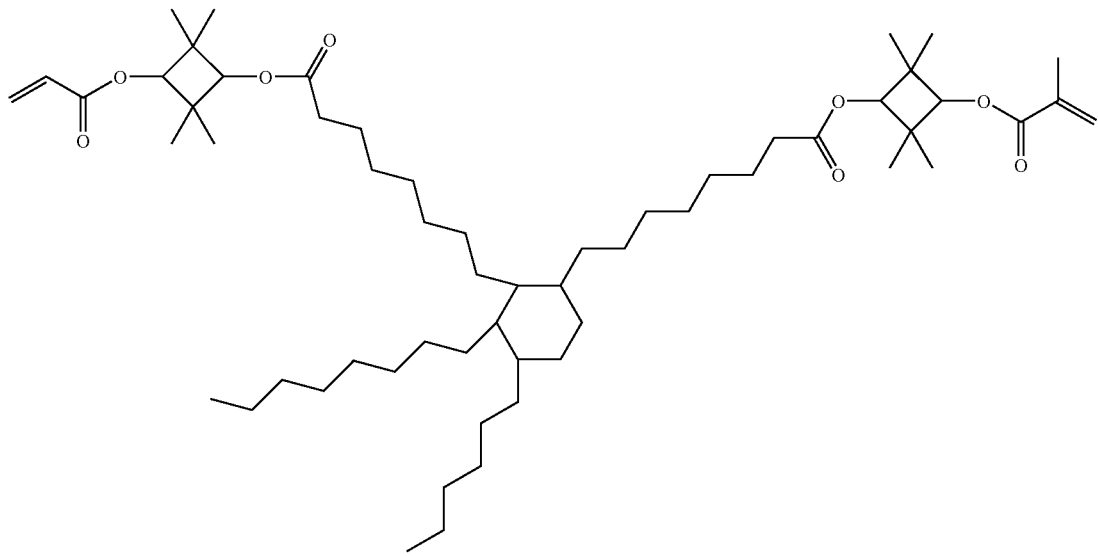
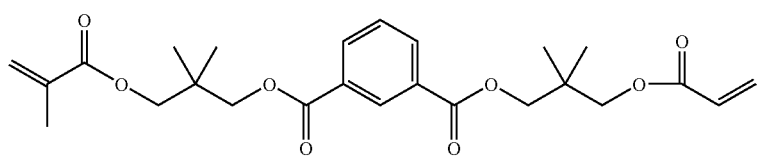
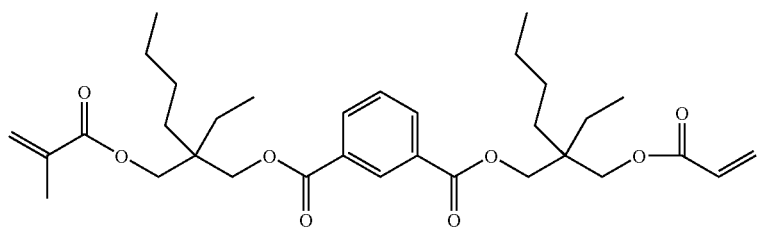
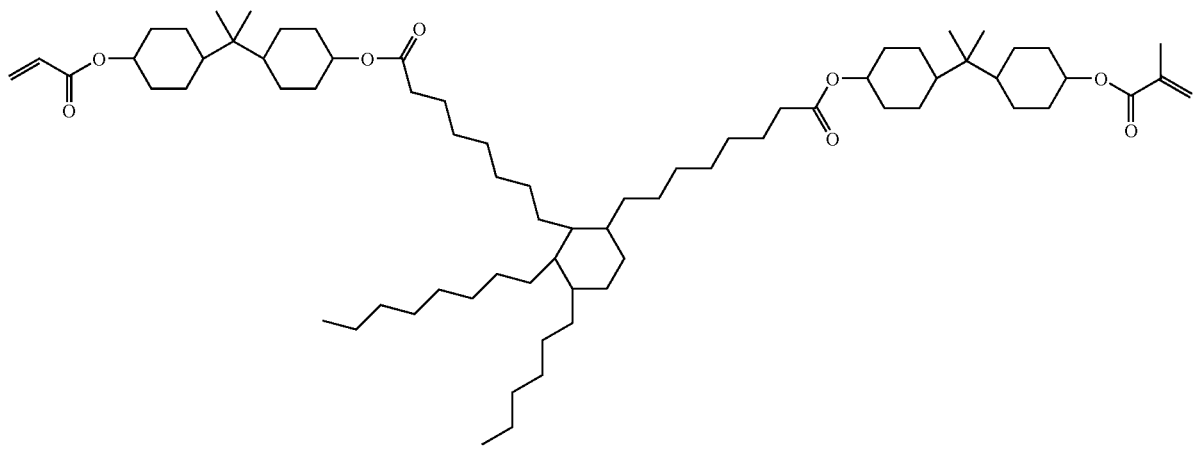

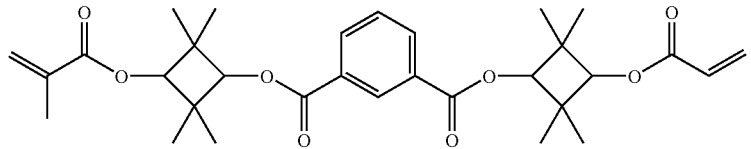
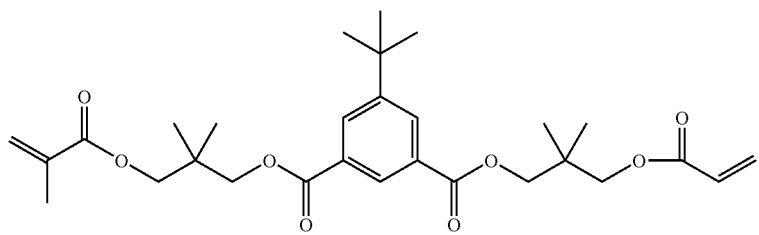
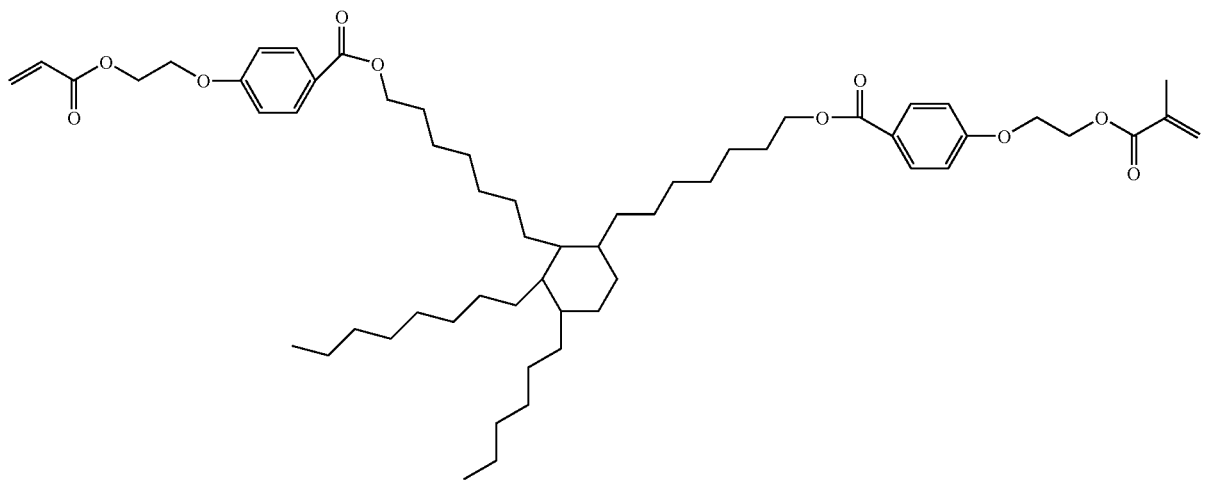
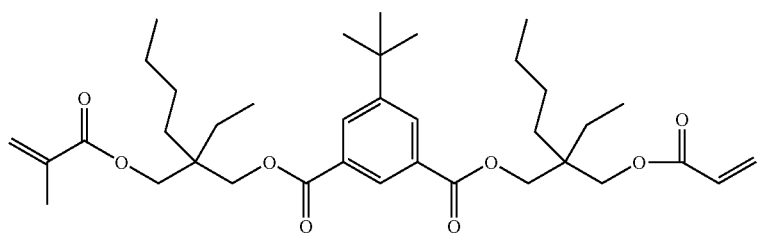
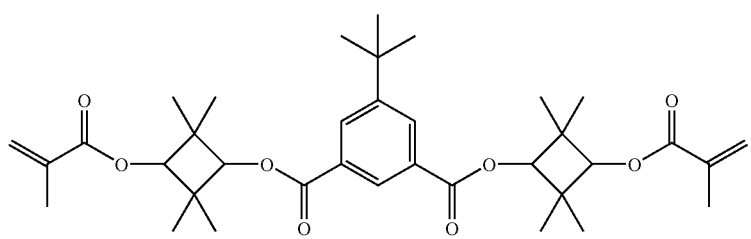

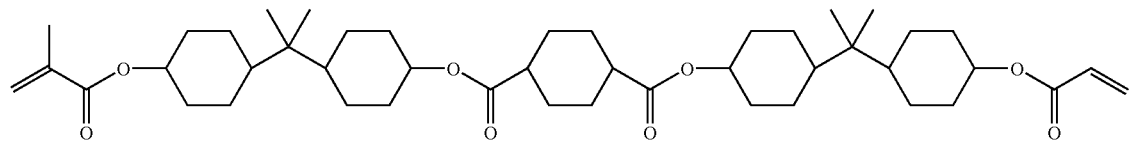
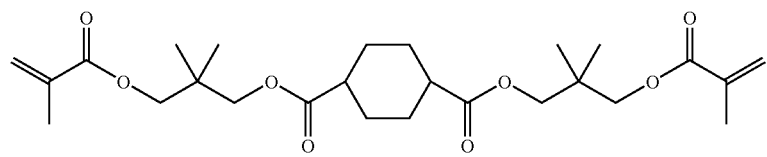
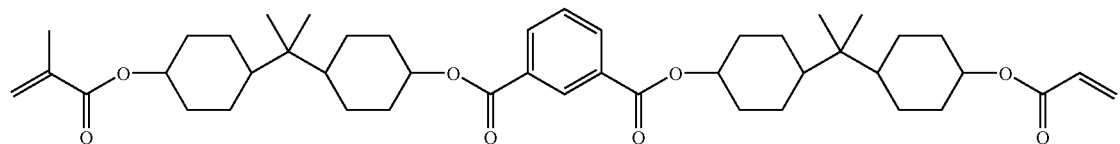
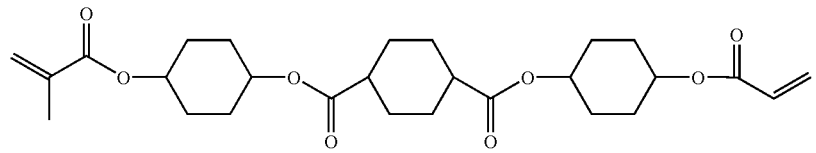
Still further examples of invention compounds include:
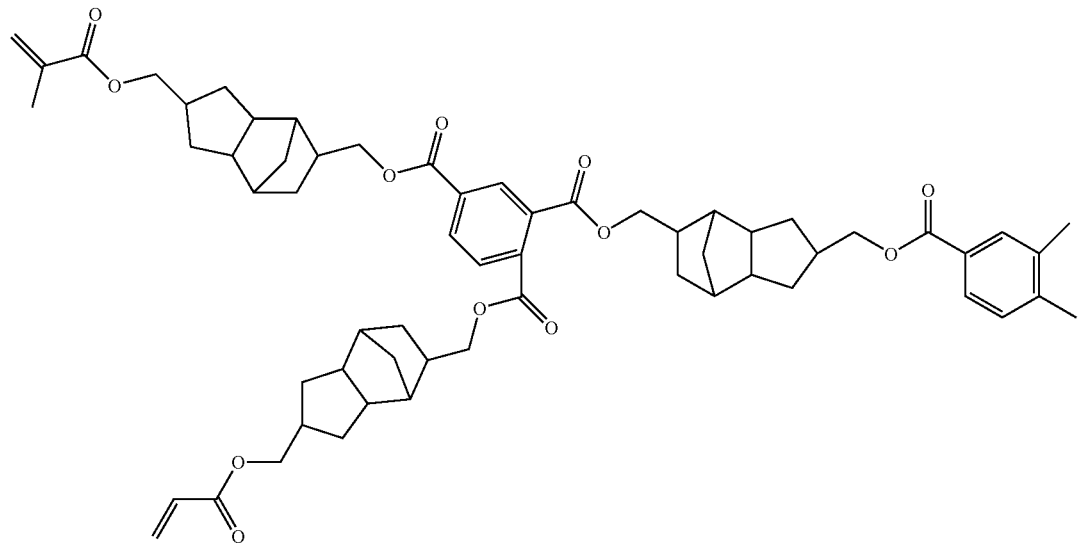

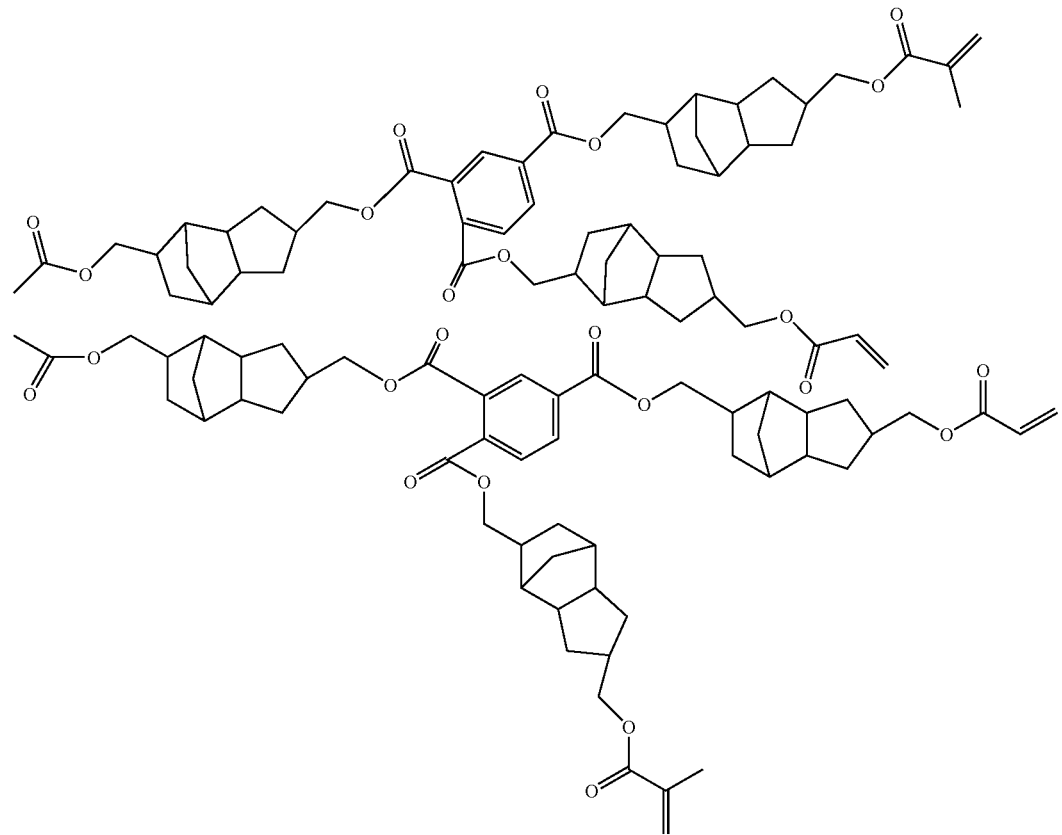
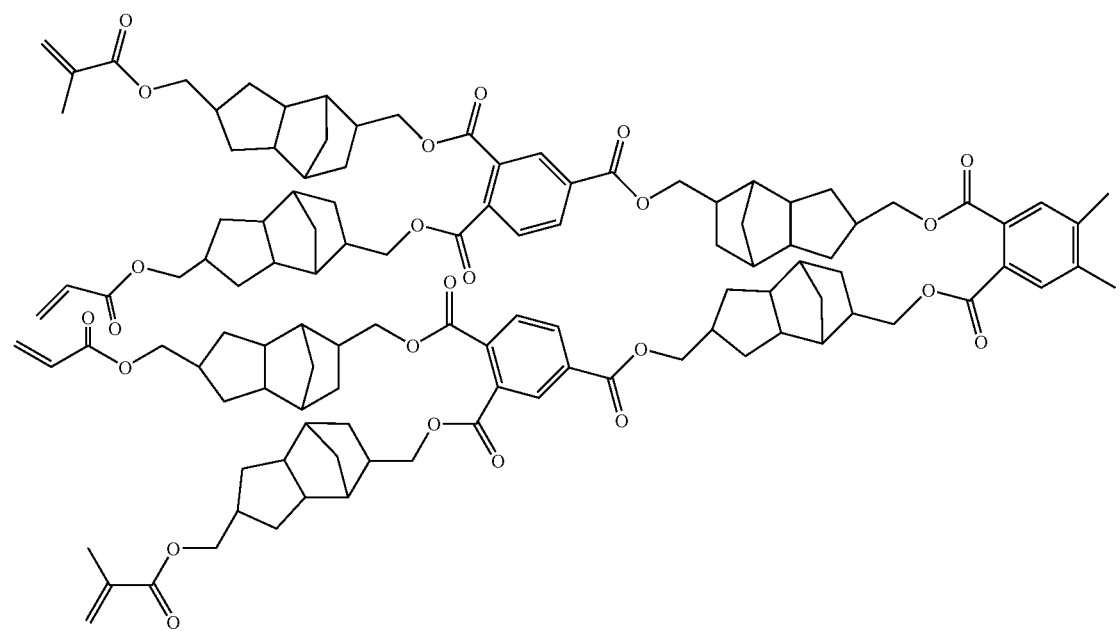

-continued

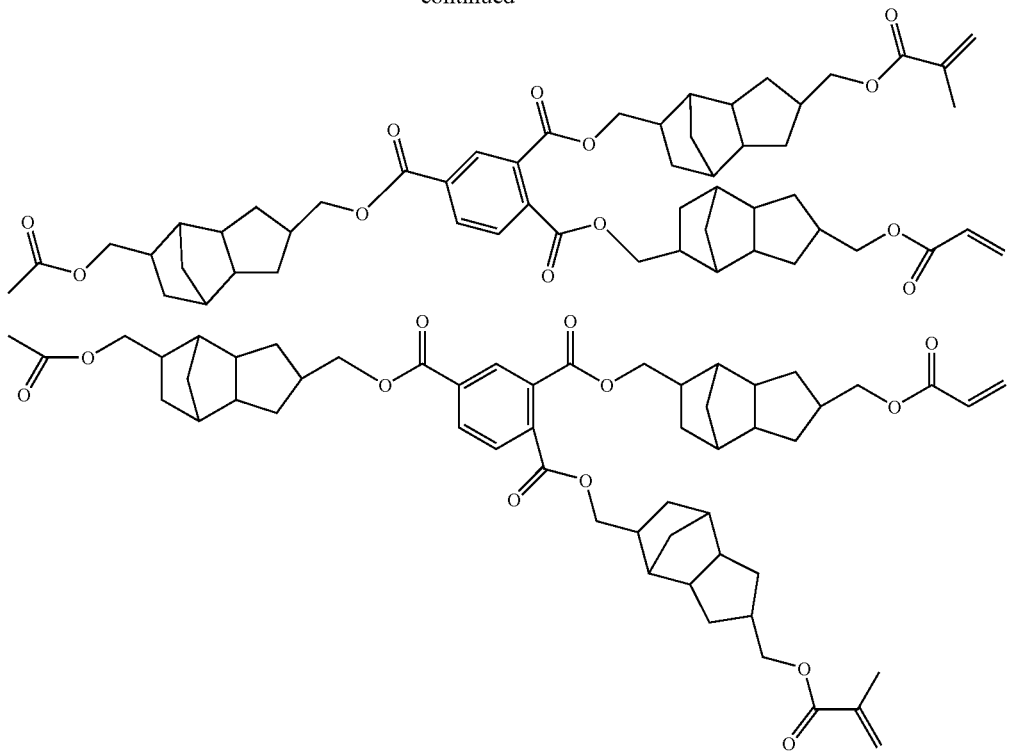

The compounds of the invention are readily prepared according to organic chemistry techniques well-known to those skilled in the art. For example, the esters described herein are typically prepared by conversion of the acid to the corresponding ester under acid catalysis. Alternatively, they can be made via transesterification via acid or base catalysis.

The polyester compounds of the invention may be used independently in adhesive compositions, or may be combined with other adhesive compounds and resins. In one embodiment, a polyester compound of the invention may be used as the sole thermoset monomer of the adhesive composition. In another embodiment, the polyester compound of the invention may be combined with other thermoset monomers to make a fully formulated adhesive.

In one embodiment, there is provided an adhesive composition including at least one polyester compound of the invention and at least one curing initiator.

In some embodiments, the polyester compound is present in the composition from 0.05 weight percent to about 98 weight percent (wt %) based on total weight of the composition. In other embodiments, there is at least one co-monomer typically present in the composition from 0.05 wt % to about 90 wt % based on total weight of the composition. Such comonomers include, for example, acrylates, methacrylates, maleimides, vinyl ethers, vinyl esters, styrenic compounds, allyl functional compounds, olefins, epoxies, oxetanes, benzoxazines, anhydrides, phenyl acetates, phenols, and the like;

The at least one curing initiator is typically present in the composition from 0.1 wt % to about 5 wt % based on total weight of the composition, and is typically a free-radical initiator. As used herein, the term "free radical initiator" refers to any chemical species which, upon exposure to sufficient energy (e.g., light, heat, or the like), decomposes into two parts which are uncharged, but which each possess at least one unpaired electron. Preferred free radical initiators contemplated for use in the practice of the present invention are compounds which decompose (i.e., have a half life in the range of about 10 hours) at temperatures in the range of about 70° C. up to 180° C. Exemplary free radical initiators contemplated for use in the practice of the present invention include peroxides (e.g., dicumyl peroxide, dibenzoyl peroxide, 2-butanone peroxide, tert-butyl perbenzoate, di-tert-butyl peroxide, 2,5-bis(tert-butylperoxy)-2,5-dimethylhexane, bis(tert-butyl peroxyisopropyl)benzene, and tert-butyl hydroperoxide), azo compounds (e.g., 2,2'-azobis(2-methylpropanenitrile), 2,2'-azobis(2-methylbutanenitrile), and 1,1'-azobis(cyclohexanecarbonitrile)), and the like.

The term "free radical initiator" also includes photoinitiators. For example, for invention adhesive compositions that contain a photoinitiator, the curing process can be initiated by UV radiation. In one embodiment, the photoinitiator is present at a concentration of 0.1 wt % to 5 wt % based on the total weight of the organic compounds in the composition (excluding any filler). In a one embodiment, the photoinitiator comprises 0.1 wt % to 3.0 wt %, based on the total weight of the organic compounds in the composition. Photoinitiators include benzoin derivatives, benzilketals, α,α-dialkoxyacetophenones, α-hydroxyalkylphenones, α-aminoalkylphenones, acylphosphine oxides, titanocene compounds, combinations of benzophenones and amines or Michler's ketone, and the like.

In another embodiment of the invention, there are provided die-attach pastes including 0.05 weight percent to about 98 weight percent (wt %) of at least one polyester compound described herein, or combinations thereof, based on total weight of the composition; optionally, 10 wt % to about 90 wt % of at least one additional compound selected from the group consisting of acrylates, methacrylates, maleimides, vinyl ethers, vinyl esters, styrenic compounds, olefins, allyl functional compounds, and the like, based on total weight of the composition; 0 to about 90 wt % of a conductive filler; 0.1 wt % to about 5 wt % of at least one curing initiator, based on total weight of the composition; and 0.1 wt % to about 4 wt %, of at least one coupling agent, based on total weight of the composition. In some embodiments, the additional compound includes, for example, epoxies (such as phenolics, novalacs (both phenolic and cresolic) and the like), imides, monomaleimides, bismaleimides, polymaleimides, cyanate esters, vinyl ethers, vinyl esters, olefins, siloxanes, cyanoacrylates, styrenics, and the like, or combinations thereof.

As used herein, "b-stageable" means that the adhesive has a first solid phase followed by a rubbery stage at elevated temperature, followed by yet another solid phase at an even higher temperature. The transition from the rubbery stage to the second solid phase is thermosetting. However, prior to that, the material behaves similarly to a thermoplastic material. Thus, such an adhesive allows for low lamination temperatures while providing high thermal stability.

The b-stageable adhesive can be dispensed onto a die or a substrate by a variety of methods well known to those skilled in the art. In some embodiments, the adhesive is cast from solution using techniques such as spin coating, spray coating, stencil printing, screen printing, and the like.

In certain embodiments, the choice of solvent or solvent system may play an important role in the dispensing characteristics of the b-stageable adhesive. For example, when the b-stageable adhesive is spin coated onto a circular wafer, it is desirable to have an even coating throughout the entire wafer, i.e., the solvent or solvent system should have the ability to deliver the same amount of adhesive to each point on the wafer. Thus, the adhesive will be evenly coated throughout, i.e., there will be the same amount of material at the center of the wafer as at the edges. Ideally, the adhesive is "Newtonian", with a slope of 1.0. In certain embodiments, the solvent or solvent systems used to dispense the b-stageable adhesive have slopes ranging from 1.0 to about 1.2.

In some instances, the b-stageable adhesive is dispensed onto a die that has been coated with a polyimide. Thus, the solvent or solvent system used to dispense the b-stageable adhesive should not have any deleterious effects on the polyimide coating. To achieve this goal, in certain embodiments, the solvent system will include a polar solvent in combination with a nonpolar solvent. Typically, the polar solvent is a good solvent for the polyester compound used as the b-stageable adhesive, and the nonpolar solvent is a non-solvent for the polyester compound. In addition, the polar solvent typically has a lower boiling point than the non-polar solvent. Without wishing to be bound by theory, it is believed that when the adhesive is dispensed and then b-staged, the lower boiling polar solvent escapes first, leaving behind only the non-polar non-solvent, essentially precipitating the polymer uniformly and leaving the polyimide film undamaged.

In some embodiments, the solvent or solvent system has a boiling point ranging from about 150° C. up to about 300° C. In some embodiments, the solvent system is a combination of dimethyl phthalate (DMP), NOPAR 13, and terpineol. In other embodiments, the solvent system is a 1:1 (by volume) ratio of terpineol and NOPAR 13.

Fillers contemplated for use in the practice of the present invention can be electrically conductive and/or thermally conductive, and/or fillers which act primarily to modify the rheology of the resulting composition. Examples of suitable electrically conductive fillers which can be employed in the practice of the present invention include silver, nickel, copper, aluminum, palladium, gold, graphite, metal-coated graphite (e.g., nickel-coated graphite, copper-coated graphite, and the like), and the like. Examples of suitable thermally conductive fillers which can be employed in the practice of the present invention include graphite, aluminum nitride, silicon carbide, boron nitride, diamond dust, alumina, boron nitride, and the like. Compounds which act primarily to modify rheology include silica, fumed silica, alumina, titania, calcium carbonate, and the like.

As used herein, the term "coupling agent" refers to chemical species that are capable of bonding to a mineral surface and which also contain polymerizably reactive functional group(s) so as to enable interaction with the adhesive composition. Coupling agents thus facilitate linkage of the die-attach paste to the substrate to which it is applied.

Exemplary coupling agents contemplated for use in the practice of the present invention include silicate esters, metal acrylate salts (e.g., aluminum methacrylate), titanates (e.g., titanium methacryloxyethylacetoacetate triisopropoxide), or compounds that contain a copolymerizable group and a chelating ligand (e.g., phosphine, mercaptan, acetoacetate, and the like). In some embodiments, the coupling agents contain both a co-polymerizable function (e.g., vinyl moiety, acrylate moiety, methacrylate moiety, and the like), as well as a silicate ester function. The silicate ester portion of the coupling agent is capable of condensing with metal hydroxides present on the mineral surface of substrate, while the co-polymerizable function is capable of co-polymerizing with the other reactive components of invention die-attach paste. In certain embodiments coupling agents contemplated for use in the practice of the invention are oligomeric silicate coupling agents such as poly(methoxyvinylsiloxane).

In some embodiments, both photoinitiation and thermal initiation may be desirable. For example, curing of a photo-initiator-containing adhesive can be started by UV irradiation, and in a later processing step, curing can be completed by the application of heat to accomplish a free-radical cure. Both UV and thermal initiators may therefore be added to the adhesive composition.

In general, these b-stageable compositions will cure within a temperature range of 80-220° C., and curing will be effected within a length of time of less than 1 minute to 60 minutes. The b-stageable die-attach paste may be preapplied onto either a semiconductor die or onto a substrate. As will be understood by those skilled in the art, the time and temperature curing profile for each adhesive composition will vary, and different compositions can be designed to provide the curing profile that will be suited to the particular industrial manufacturing process.

In certain embodiments, the adhesive compositions may contain compounds that lend additional flexibility and toughness to the resultant cured adhesive. Such compounds may be any thermoset or thermoplastic material having a $T_g$ of 50° C. or less, and typically will be a polymeric material characterized by free rotation about the chemical bonds, the presence of ether groups, and the absence of ring structures. Suitable such modifiers include polyacrylates, poly(butadiene), poly-THF (polymerized tetrahydrofuran, also known as poly(1,4-butanediol)), CTBN (carboxy-terminated butadiene-acrylonitrile) rubber, and polypropylene glycol. When present, toughening compounds may be in an amount up to about 15 percent by weight of the maleimide and other monofunctional vinyl compound.

Inhibitors for free-radial cure may also be added to the adhesive compositions and die-attach pastes described herein to extend the useful shelf life of compositions containing the polyester linked acrylates and methacrylates. Examples of these inhibitors include hindered phenols such as 2,6-di-tert-butyl-4-methylphenol; 2,6-di-tert-butyl-4-methoxyphenol; tert-butyl hydroquinone; tetrakis(methylene(3,5-di-tert-butyl-4-hydroxyhydrocinnamate))benzene; 2,2'-methylenebis (6-tert-butyl-p-cresol); and 1,3,5-trimethyl-2,4,6-tris(3',5'-di-tert-butyl-4-hydroxybenzyl)benzene. Other useful hydrogen-donating antioxidants include derivatives of p-phenylenediamine and diphenylamine. It is also well know in the art that hydrogen-donating antioxidants may be synergistically combined with quinones, and metal deactivators to make a very efficient inhibitor package. Examples of suitable quinones include benzoquinone, 2-tert butyl-1,4-benzoquinone; 2-phenyl-1,4-benzoquinone; naphthoquinone, and 2,5-dichloro-1,4-benzoquinone. Examples of metal deactivators include N,N'-bis(3,5-di-tert-butyl-4-hydroxyhydrocinnamoyl)hydrazine; oxalyl bis(benzylidenehydrazide); and N-phenyl-N'-(4-toluenesulfonyl)-p-phenylenediamine.

Nitroxyl radical compounds such as TEMPO (2,2,6,6-tetramethyl-1-piperidnyloxy, free radical) are also effective as inhibitors at low concentrations. The total amount of antioxidant plus synergists typically falls in the range of 100 to 2000 ppm relative to the weight of total base resin. Other additives, such as adhesion promoters, in types and amounts known in the art, may also be added.

These compositions will perform within the commercially acceptable range for die attach adhesives. Commercially acceptable values for die shear for the adhesives on a 80×80 mil$^2$ silicon die are in the range of greater than or equal to 1 kg at room temperature, and greater than or equal to 0.5 kg at 260° C.

In yet another embodiment of the invention, there are provided assemblies of components adhered together employing the above-described b-stageable adhesive compositions and/or die attach pastes. Thus, for example, assemblies comprising a first article permanently adhered to a second article by a cured aliquot of the above-described adhesive composition are provided. Articles contemplated for assembly employing invention compositions include memory devices, ASIC devices, microprocessors, flash memory devices, and the like. Also contemplated are assemblies comprising a microelectronic device permanently adhered to a substrate by a cured aliquot of the above-described die attach paste. Microelectronic devices contemplated for use with invention die attach pastes include copper lead frames, Alloy 42 lead frames, silicon dice, gallium arsenide dice, germanium dice, and the like.

Conditions suitable to cure invention die attach pastes include subjecting the above-described assembly to a temperature of less than about 200° C. for about 0.5 up to 2 minutes. This rapid, short duration heating can be accomplished in a variety of ways, e.g., with an in-line heated rail, a belt furnace, or the like. Optionally, the material can be oven cured at 150-220° C.

In another embodiment of the invention, there are provided methods for adhesively attaching a first article to a second article. Such methods can be performed, for example, by (a) applying an aliquot of the adhesive composition of the invention to the first article, (b) bringing the first and second article into intimate contact to form an assembly wherein the first article and the second article are separated only by the adhesive composition applied in (a), and (c) subjecting the assembly to conditions suitable to cure the adhesive composition.

In another embodiment of the invention, there are provided methods for adhesively attaching a semiconductor die to a substrate. Such methods can be performed, for example, by (a) applying the b-stageable die attach paste of the invention to the substrate and/or the microelectronic device, (b) subjecting the substrate and/or the microelectronic device to conditions suitable to form a b-staged curable film, (c) exposing the b-staged curable film to temperature conditions suitable to melt the film, (d) bringing the substrate and the device into intimate contact to form an assembly wherein the substrate and the device are separated only by the die-attach paste, and (e) subjecting the b-staged curable film to conditions suitable to cure the melted film.

It is understood that using the compounds and methods of the present invention, it is possible to prepare adhesives having a wide range of cross-link density by the judicious choice and amount of polyester compounds. The greater proportion of polyfunctional compounds reacted, the greater the cross-link density. If thermoplastic properties are desired, the adhesive compositions can be prepared from (or at least contain a higher percentage of) mono-functional compounds to limit the cross-link density. A minor amount of poly-functional compounds can be added to provide some cross-linking and strength to the composition, provided the amount of poly-functional compounds is limited to an amount that does not diminish the desired thermoplastic properties. Within these parameters, the strength and elasticity of individual adhesives can be tailored to a particular end-use application.

"Cross-linking," as used herein, refers to the attachment of two or more polymer chains by bridges of an element, a molecular group, or a compound. In general, crosslinking of the compounds of the invention takes place upon heating. As cross-linking density is increased, the properties of a material can be changed from thermoplastic to thermosetting.

EXAMPLES

Example 1

The following describes an exemplary synthesis of a polyester linked acrylate or methacrylate according to the invention.

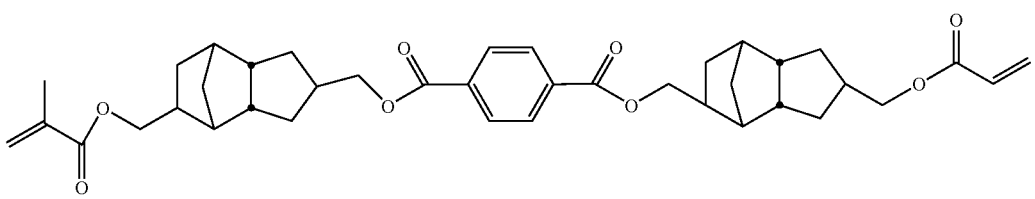

A 500 mL round-bottomed flask was charged with terephthalic acid (8.31 g, 50 mmol), tricyclodecane-dimethanol (23.6 g, 120 mmol), toluene (110 g), and methanesulfonic acid (3.5 g). This mixture was refluxed for 1.5 hours, at which time 2.0 mL of water was collected in a Dean-Stark trap. Next, acrylic acid (7.23 g, 100 mmol) and methacrylic acid (8.62 g, 100 mmol) and an additional 200 mL of toluene were added to the reaction flask. This mixture was refluxed for 2.25 hours, at which time 2.3 mL water had collected in the Dean-Stark trap. This material was then worked up with NaHCO$_3$ (25 g) and 3.5 g water followed by 21 g MgSO$_4$. Once all gas evolution had ceased, the solution was passed through silica gel and the toluene was removed by rotary evaporation, affording the product (36.6 g, 95% yield).

Example 2

(23.6 g, 120 mmol), toluene (110 g), and methanesulfonic acid (3.5 g). This mixture was refluxed for 1.5 hours, at which time 2.0 mL of water was collected in a Dean-Stark trap. Next, acrylic acid (7.23 g, 100 mmol) and methacrylic acid (8.62 g, 100 mmol) and an additional 200 mL of toluene were added to the reaction flask. This mixture was refluxed for 2.5 hours, at which time 2.3 mL water had collected in the Dean-Stark trap. This material was then worked up with NaHCO$_3$ (25 g) and 3.5 g water followed by 21 g MgSO$_4$. Once all gas evolution had ceased, the solution was passed through silica gel and the toluene was removed by rotary evaporation, affording the product (36.6 g, 95% yield).

Example 3

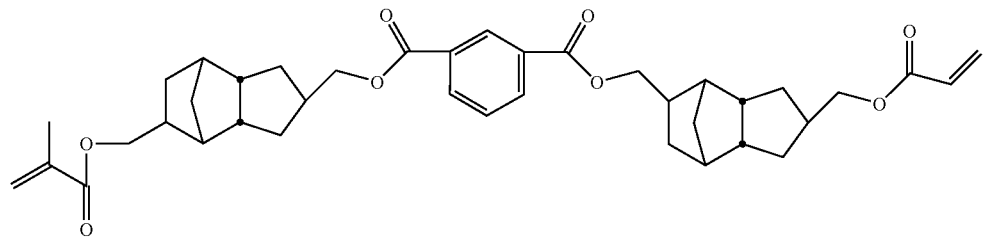

A 500 mL round bottomed flask was charged with isophthalic acid (8.31 g, 50 mmol), dicyclopentadiene-dimethanol

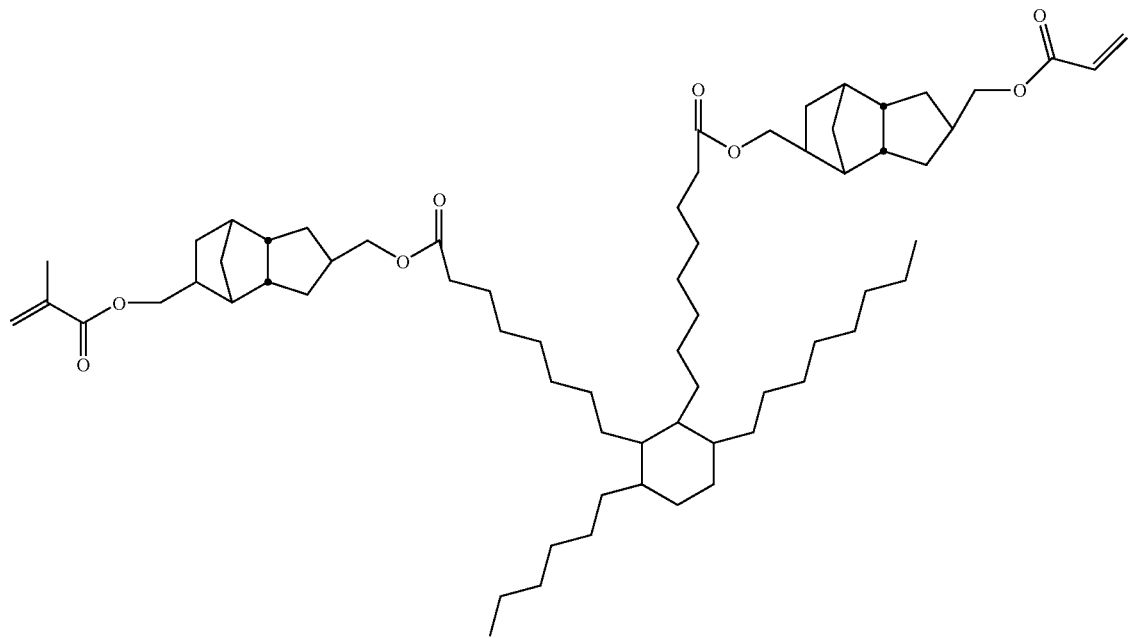

A 500 mL round bottomed flask was charged with dimer acid Cognis Empol 1008 (28.27 g, 50 mmol), dicyclopentadiene-dimethanol (23.6 g, 120 mmol), toluene (110 g), and methanesulfonic acid (3.5 g). This mixture was refluxed for 0.5 hours, at which time 2.0 mL of water was collected in a Dean-Stark trap. Next, acrylic acid (7.23 g, 100 mmol) and methacrylic acid (8.62 g, 100 mmol) and an additional 200 mL of toluene were added to the reaction flask. This mixture was refluxed for 2.5 hours, at which time 2.1 mL water had collected in the Dean-Stark trap. This material was then worked up with NaHCO$_3$ (25 g) and 3.5 g water followed by 21 g MgSO$_4$. Once all gas evolution had ceased, the solution was passed through silica gel and the toluene was removed by rotary evaporation, affording the product (54.6 g, 93% yield).

Branched TCD Dimethanol Ester Triol Precursor. A triol approximately corresponding to the above structure was prepared. A 500 mL, two-neck flask was charged with 38.43 g (0.2 mole) 1,2,4-benzenetricarboxylic anhydride, 117.6 g (0.6 mole) tricyclodecane dimethanol, and 50 mL toluene. This mix was heated and controlled at 165° C. (about 35 mL toluene was removed to allow the reflux to attain this temperature) under an argon blanket. Water condensate was collected in a Dean-Stark trap. The reaction was continued for nineteen hours and the theoretical amount of water (7.2 mLs) was collected. Most of the remaining toluene was removed by sparging the mix with argon at 165° C. for forty minutes. The product was poured out while still hot onto non-stick aluminum foil. It turned to a clear, light yellow glassy solid upon cooling to room temperature. It weighed 154.2 grams (103% of theory . . . some residual toluene remained in the product). An FTIR run on this material showed strong absorptions at 3343, 2944, 1722, 1284, 1237, 1115, and 730 wavenumbers.

Example 4

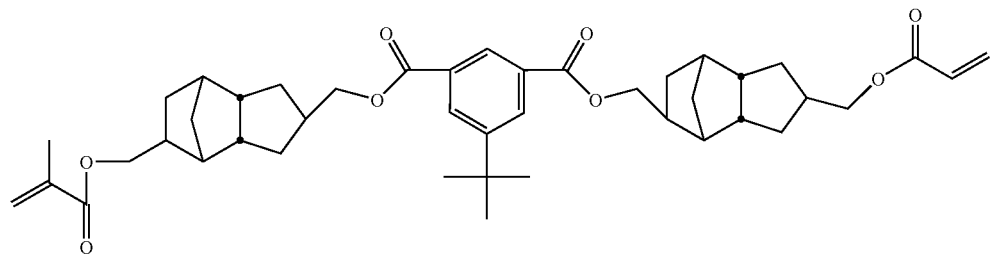

A 500 mL round bottomed flask was charged with 5-t-butyl-isophthalic acid (11.2 g, 50 mmol), tricyclodecane-dimethanol (23.6 g, 120 mmol), toluene (110 g), and methane sulfonic acid (1.0 g). This mixture was refluxed for 2 hours, at which time 1.8 mL of water was collected in a Dean-Stark trap. Next, acrylic acid (7.23 g, 100 mmol), methacrylic acid (8.62 g, 100 mmol), methanesulfonic acid (1.5 g), and an additional 120 mL of toluene were added to the reaction flask. This mixture was refluxed for 2.5 hours, at which time 2.3 mL water had collected in the Dean-Stark trap. This material was then worked up with NaHCO$_3$ (25 g) and 3.5 g water followed by 21 g MgSO$_4$. Once all gas evolution had ceased, the solution was passed through silica gel and the toluene was removed by rotary evaporation, affording the product (39.8 g, 96% yield).

Example 5

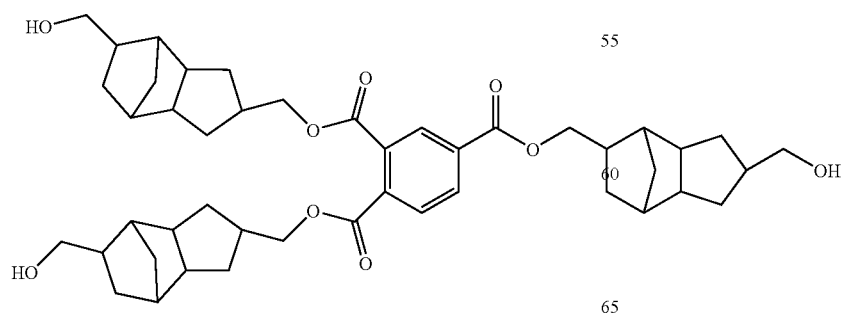

Example 6

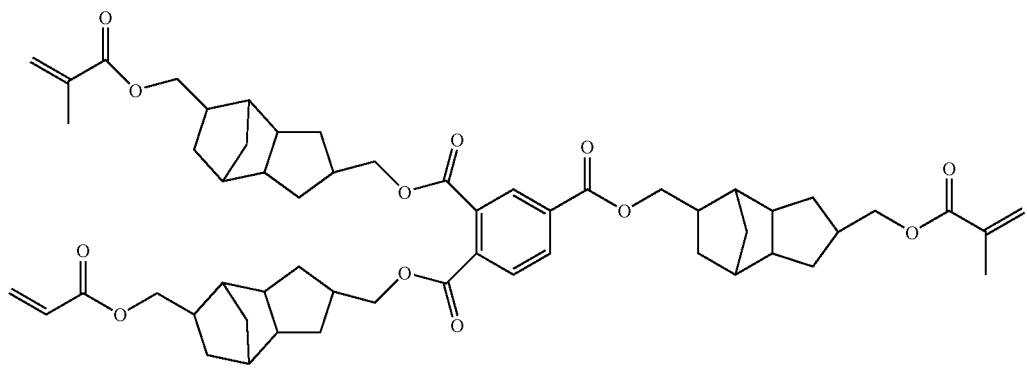

Trifunctional (Meth)acrylate of Example 5. A 500 mL, two-neck flask was charged with 67.0 g (approximately, 0.09 mole) of the triol from example 1, 200 mL toluene, 17.2 g (0.2 mole) methacrylic acid, 7.21 g (0.1 mole) acrylic acid, 170 mg hydroquinone and 1.5 g methanesulfonic acid. This mix was refluxed under an air sparge for three hours and 4.6 mLs water was collected in the trap. The residual acid was neutralized by stirring the mix with 15 g sodium bicarbonate and 3 g water, until carbon dioxide evolution ceased. The mix was dried with ten grams magnesium sulfate and then passed over twenty grams of silica gel. The toluene was removed to yield 78.14 g (83.6% of theory) of a sticky, viscous amber liquid. The FTIR spectrum had prominent absorptions at 2947, 1714, 1637, 1293, 1236, 1161, 1114, 1064, 942, and 811 wavenumbers. A TGA (10° C./min. to 550° C., air purge) was run on this material with and without 2% dicumyl peroxide catalyst. The retained weight at 300° C. was 97.2% for the catalyzed sample and 92.4% for the uncatalyzed. The decomposition onset was 412° C.

Example 7

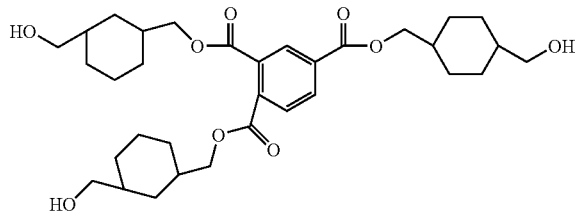

Branched Cyclohexanedimethanol Ester Triol Precursor. A triol approximately corresponding to the above structure was prepared. A 500 mL, two-neck flask was charged with 38.43 g (0.2 mole) 1,2,4-benzenetricarboxylic anhydride, 86.53 g (0.6 mole) Unoxol Diol (1,4- and 1,3-dimethanolcycylohexanes from Dow Chemical), and 50 mL toluene. This mix was heated and controlled at 165° C. (about 35 mL toluene was removed to allow the reflux to attain this temperature) under an argon blanket. Water condensate was collected in a Dean-Stark trap. The reaction was continued for three hours and 7.4 mL water (7.2 mL=theory) was collected. Most of the remaining toluene was removed by sparging the mix with argon at 165° C. for forty minutes. The product was poured out while still hot onto non-stick aluminum foil. It turned to a clear, almost colorless glassy solid upon cooling to room temperature. An FTIR run on this material showed strong absorptions at 3344, 2925, 1725, 1279, 1249, 1114, and 752 wavenumbers.

Example 8

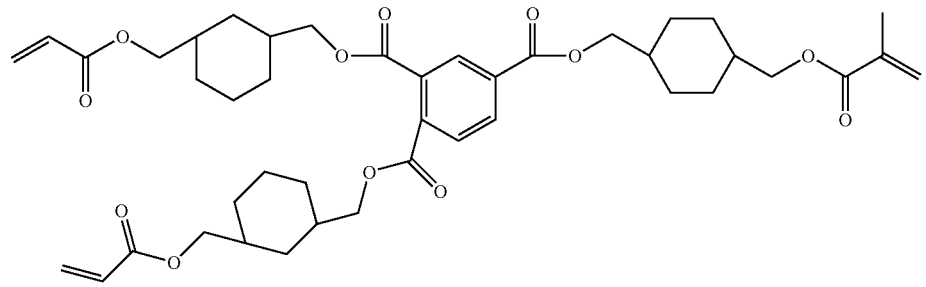

Trifunctional (Meth)acrylate of Example 7. A 500 mL, three-neck flask was charged with 58.87 g (approximately, 0.1 mole) of the triol from example 1, 200 mL toluene, 10.76 g (0.125 mole) methacrylic acid, 18.0 g (0.25 mole) acrylic acid, 300 mg hydroquinone and 2.0 g methanesulfonic acid. This mix was refluxed under an air sparge for two hours and 5.3 mLs water was collected in the trap. The mix was worked up as in Example 2 to yield 71.2 g (91.4% of theory) of a viscous, light yellow liquid. A TGA (10° C./min. to 550° C., air purge) was run on this material with and without 2% dicumyl peroxide catalyst. The retained weight at 300° C. was 97.0% for the catalyzed sample and 85.5% for the uncatalyzed. The decomposition onset was 413° C. A TMA was run on a cured sample of this material and the glass transition temperature was found to be 148.0° C., the $\alpha_1$=55.9 ppm° C.$^{-1}$ and the $\alpha_2$=150.7 ppm° C.$^{-1}$.

lected. The solution was cooled to below 50° C. and the flask was charged with 43.1 g (0.28 moles) methacrylic anhydride, 107 mg BHT, 0.5 g DMAP, and another 100 mL toluene. This mix was then stirred at 80° C. for twenty-six hours. All of the anhydride had disappeared according to an FTIR scan. The toluene soluble phase was extracted three times with 50 mLs DI water. The mix was then neutralized with 15 g sodium bicarbonate, dried with 12 g magnesium sulfate and passed over 25 g silica gel. The toluene was removed to yield 113.2 g (94.3% of theory) of a clear yellow liquid. The viscosity of this liquid was 16,364 cps at 25° C. The residual weight (catalyzed with 2% dicup) was 95.2% and the decomposition onset was 328° C. (both via TGA at 10° C./min. with an air purge). The FTIR trace had major peaks at 2925, 2853, 1714, 1638, 1161, and 938 wavenumbers.

Example 9

Example 10

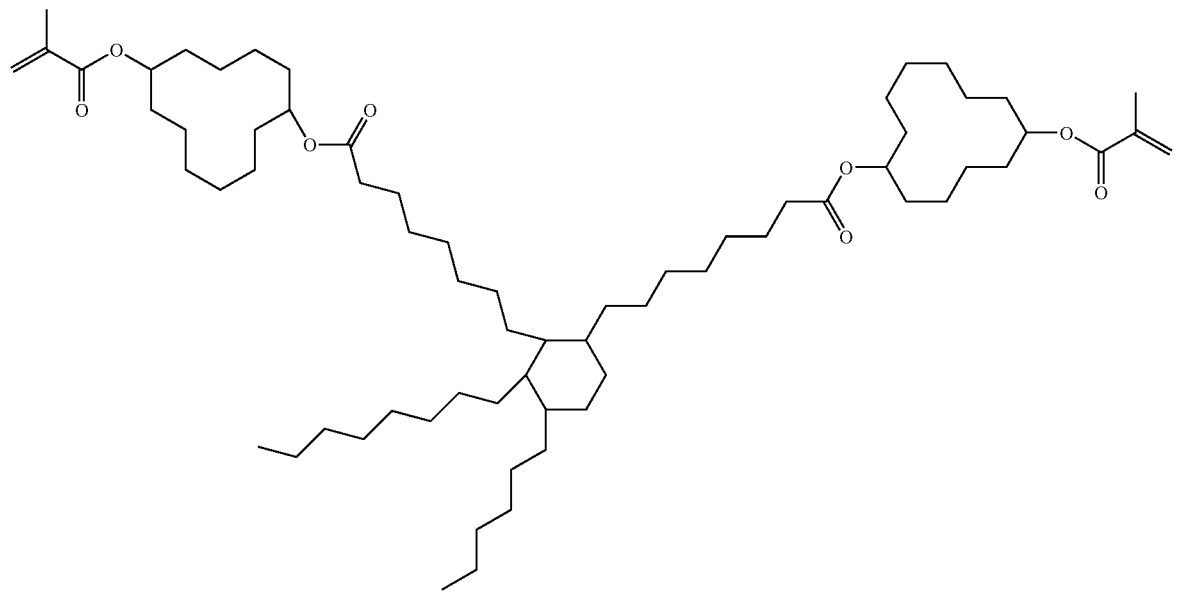

Dimer acid extended cyclododecane dimethacrylate. A 500 mL, two-neck flask was charged with 56.5 g (0.1 mole) dimer acid, 48.0 g (0.24 mole) cyclododecane diol, and 50 mL toluene. A Dean-Stark trap and condenser were attached and the mix was refluxed and stirred under an argon blanket for nine hours. A total of 3.8 mLs water (3.6=theory) was col-

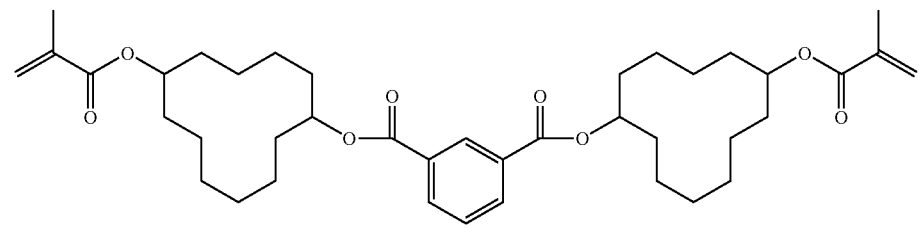

Isophthalic acid extended dodecanediol dimethacrylate. A 500 mL, 2-neck flask was charged with 48.0 g (0.24 mole) cyclododecanediol, 16.61 g (0.1 mole) isophthalic acid, and 50 mL toluene. The flask was equipped with a Dean-Stark trap and condenser. The mix was heated to 180° C. for 37 hours to remove the theoretical 3.6 mLs of water (note: about 40 mLs toluene—including what was contained in the trap had to be removed to attain the 180° C. reflux temperature). The mix was cooled to less than 50° C. and then 43.1 g (0.28 mole) methacrylic anhydride, 70 mg BHT, 0.5 g DMAP, and another 100 mL toluene was added to the flask. This mixture was stirred at 80° C. for 40 hours. The product was worked up in a fashion similar to the preceding example to give 62.8 g (79% of theory) of a clear, viscous, light yellow liquid. An FTIR was run on the product and showed major absorptions at 2942, 1714, 1637, 1295, 1238, 1163, 939, and 730 wavenumbers. A TGA run on the catalyzed (2% dicup) compound showed a residual weight of 97.4% at 200° C. and a decomposition onset of 315° C.

500 mL flask was charged with 28.84 g (0.2 mole) Unoxol Diol (Dow Chemical), 56.5 g (0.1 mole) dimer acid, 150 mL toluene, and 2.0 g methanesulfonic acid. This mix was refluxed for three hours to collect 3.6 mLs water (equal to theory). The mixture was cooled and 10.76 g (0.125 mole) methacrylic acid, 9.01 g (0.125 mole) acrylic acid, 2.0 g methanesulfonic acid, and 190 mg hydroquinone were added. This mix was refluxed again for three hours and another 3.6 mLs of water was collected. This mixture was worked up as outlined in previous examples to yield 86.6 g (92% of theory) of a clear, light yellow, liquid. The viscosity of this compound at 25° C. was 2,540 cps. An FTIR trace on the material showed major absorptions at 2922, 2853, 1727, 1637, 1453, 1188, and 810 wavenumbers. The residual weight at 300° C. (TGA, catalyzed with 2% dicup) was 96.9% and the decomposition onset was 424° C.

Example 11

Example 12

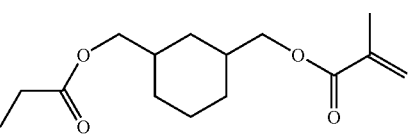

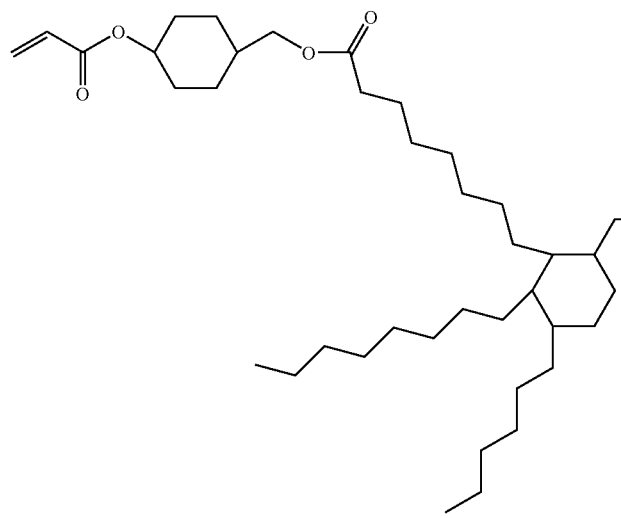

Dimer acid extended cylcohexanedimethanol (1,4- and 1,3-mixed isomers) acrylate-methacrylate. A single-neck,

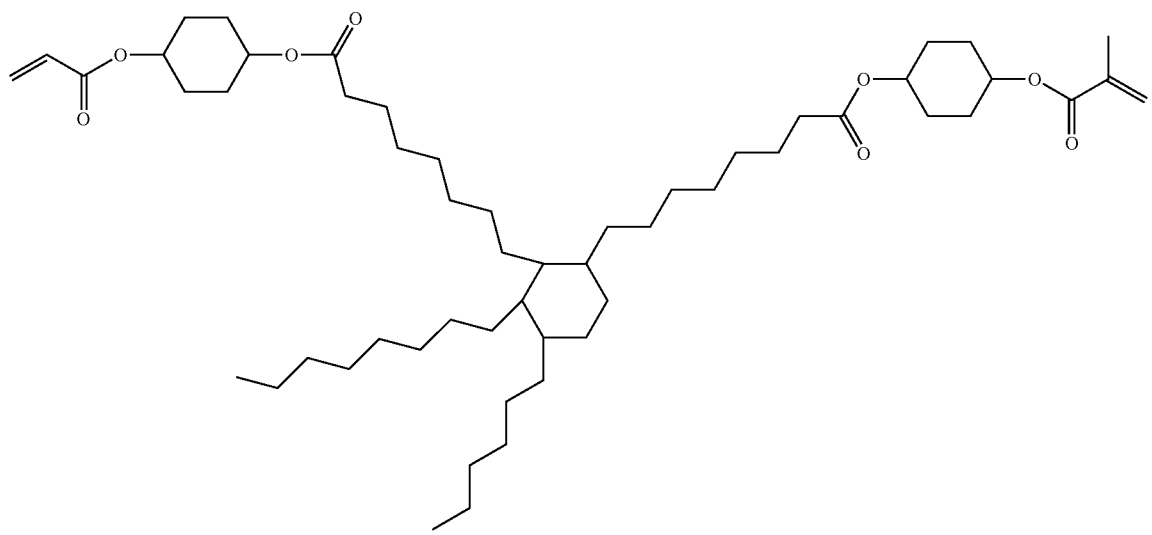

Dimer acid extended 1,4-cyclohexanediol acrylate-methacrylate. A 500 mL, two-neck flask was charged with 56.5 g (0.1 mole) dimer acid, 23.23 g (0.2 mole 1,4-cyclohexanediol), and 25 mL heptane. This mix was refluxed for 3.75 hours and 4.2 mLs water (theory=3.6). This mixture was cooled and 8.65 g (0.12 mole) acrylic acid, 10.3 g (0.12 mole) methacrylic acid, 2.0 g methanesulfonic acid, 90 mg hydroquinone, and another 150 ml of heptane were added. This mix was refluxed for 4.3 hours and another 4.5 mLs water was collected. The mix was worked up in a way similar to that in previous examples to yield 72.1 g (81.6% of theory) of a light amber liquid. An FTIR trace on this sample showed major absorptions at 2924, 2855, 1731, 1457, 1167, and 1041 wavenumbers. The retained weight at 300° C. for the catalyzed monomer was 97.1% and the decomposition onset was 365° C.

5.2 mL water (3.6=theory) was collected. The mix was cooled and then charged with 9.0 g (0.125 mole) acrylic acid, 10.76 g (0.125 mole) methacrylic acid, 2.0 g methanesulfonic acid, 55 mg hydroquinone, and another 150 mL toluene. This mix was refluxed under an air sparge and another 3.8 mLs water (3.6=theory) was collected in the trap. The material was worked up to give 49.65 g (91.8% of theory) of an almost colorless viscous liquid. The viscosity at 25° C. was 27,772 cps. The FTIR spectrum had absorptions at 2929, 1721, 1636, 1296, 1229, 1163, 981, and 730 wavenumbers. The residual weight via TGA was 98.3% at 300° C. and the decomposition onset was 428° C. A TMA was run on a cured sample of this material and the glass transition temperature was found to be 82.1° C., the $\alpha_1$=50.6 ppm° $C.^{-1}$ and the $\alpha_2$=168 ppm° $C.^{-1}$.

Example 13

Example 14

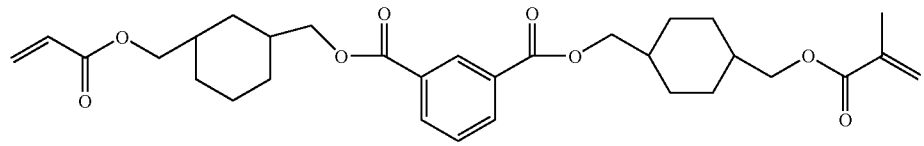

Isophthalic acid extended cyclohexanedimethanol (1,4- and 1,3-mixed isomers) acrylate-methacrylate. A 500 mL, two-neck flask was charged with 28.84 g (0.2 mole) Unoxol Diol, 16.61 g (0.1 mole) isophthalic acid and 50 mL toluene. The flask was equipped with a Dean-Stark trap and condenser and brought to reflux. About 30 mL of toluene was removed to allow the condensation to progress at a good rate. A total of

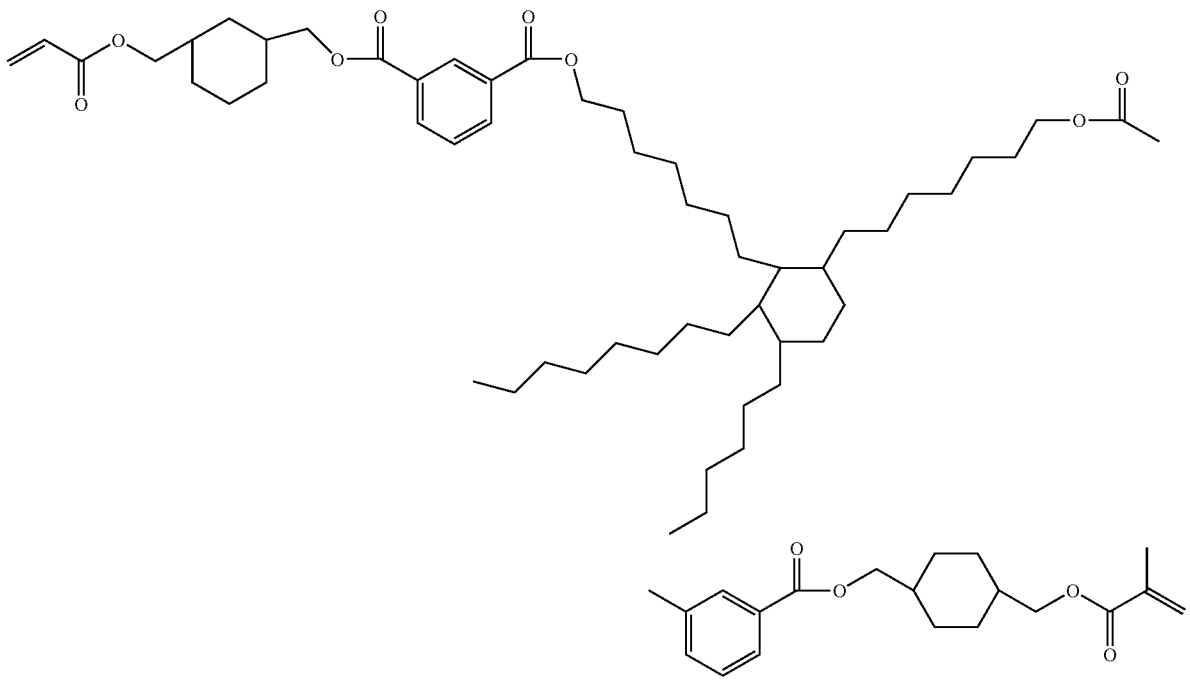

Isophthalic acid and dimerdiol extended mixed cyclohexanediol acrylate-methacrylate. A two-neck, 500 mL flask was charged with 28.84 g (0.2 mole) Unoxol Diol, 33.23 g (0.2 mole) isophthalic acid, 53.7 g (0.1 mole) dimerdiol, and 50 mL toluene. This mixture was refluxed for twenty hours at 180° C. to collect 7.0 mL water (7.2=theory). The mix was cooled and 9.0 g (0.125 mole) acrylic acid, 10.76 g (0.125 mole) methacrylic acid, 2.0 g methanesulfonic acid, 60 mg hydroquinone, and 200 mL additional toluene. This mixture was refluxed under an air sparge for 2.5 hours and 3.5 ml water (3.6=theory) was collected in the trap. The product was worked up in the usual manner to give 115.18 g (95.5% of theory) of a light amber viscous liquid. Major absorptions in the FTIR spectrum were observed at 2921, 2854, 1725, 1637, 1453, 1297, 1230, 1163, 1075, 982, and 723 wavenumbers. The uncatalyzed monomer had 97.8% retained weight at 300° C. and a decomposition onset of 422° C.

While this invention has been described with respect to these specific examples, it should be clear that other modifications and variations would be possible without departing from the spirit of this invention.

What is claimed is:

1. A compound having the structure:

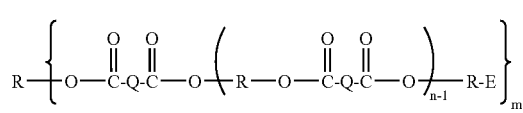

II wherein:
each of R and Q is independently selected from the group consisting of substituted or unsubstituted aliphatic, aryl and heteroaryl moieties;
m is an integer having the value of 3 or 4; and
n is integer having the value of between 1 and about 10; and
each E is independently selected from the group consisting of an acrylate, a methacrylate, maleimide, styrenic, vinyl ester, an olefin, allyl, vinyl ether, itaconate, fumarate, epoxy, oxetane, oxazoline, benzoxazine, cyanate ester and propargyl ether.

2. The compound of claim 1, wherein R is a substituted or an unsubstituted cycloalkyl having between 5 and about 20 carbon atoms.

3. The compound of claim 1, wherein R is a substituted or an unsubstituted cycloalkyl having between 5 and about 12 carbon atoms.

4. The compound of claim 1, wherein R is selected from the group consisting of a substituted cyclopentyl, an unsubstituted cyclopentyl, cyclohexyl, norbornyl, tricyclododecyl and dicyclopentadienyl.

5. The compound of claim 1, wherein Q is a substituted or an unsubstituted aryl or heteroaryl having between 6 and about 14 carbon atoms.

6. The compound of claim 1, wherein Q is selected from the group consisting of a substituted or an unsubstituted phenyl and a substituted or an unsubstituted naphthyl.

7. The compound of claim 1, wherein Q is a substituted or an unsubstituted cycloalkyl.

8. The compound of claim 1, wherein Q is a substituted or an unsubstituted norbornenyl.

9. The compound of claim 1, wherein substituted aliphatic, aryl, or heteroaryl moieties comprise substituents selected from the group consisting of an alkyl, an alkenyl, an alkynyl, hydroxy, oxo, an alkoxy, mercapto, a cycloalkyl, a substituted cycloalkyl, a heterocyclic, a substituted heterocyclic, an aryl, a substituted aryl, a heteroaryl, a substituted heteroaryl, an aryloxy, a substituted aryloxy, a halogen, a haloalkyl, cyano, nitro, nitrone, an amino, an amido, —C(O)H, —C(O)—O—, —C(O)—, —S—, —S(O)$_2$—, —OC(O)—O—, —NR—C(O)—, —NR—C(O)—NR— and —OC(O)—NR—, wherein R is selected from the group consisting of H, a lower alkyl, an acyl, an oxyacyl, carboxyl, carbamate, sulfonyl, a sulfonamide and sulfuryl.

10. The compound of claim 1, selected from the group consisting of compounds having any one of the following structures:

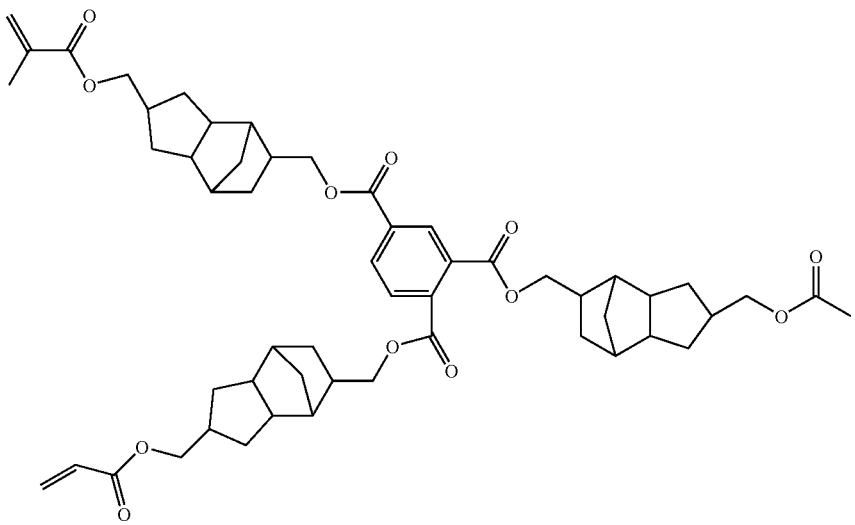

-continued
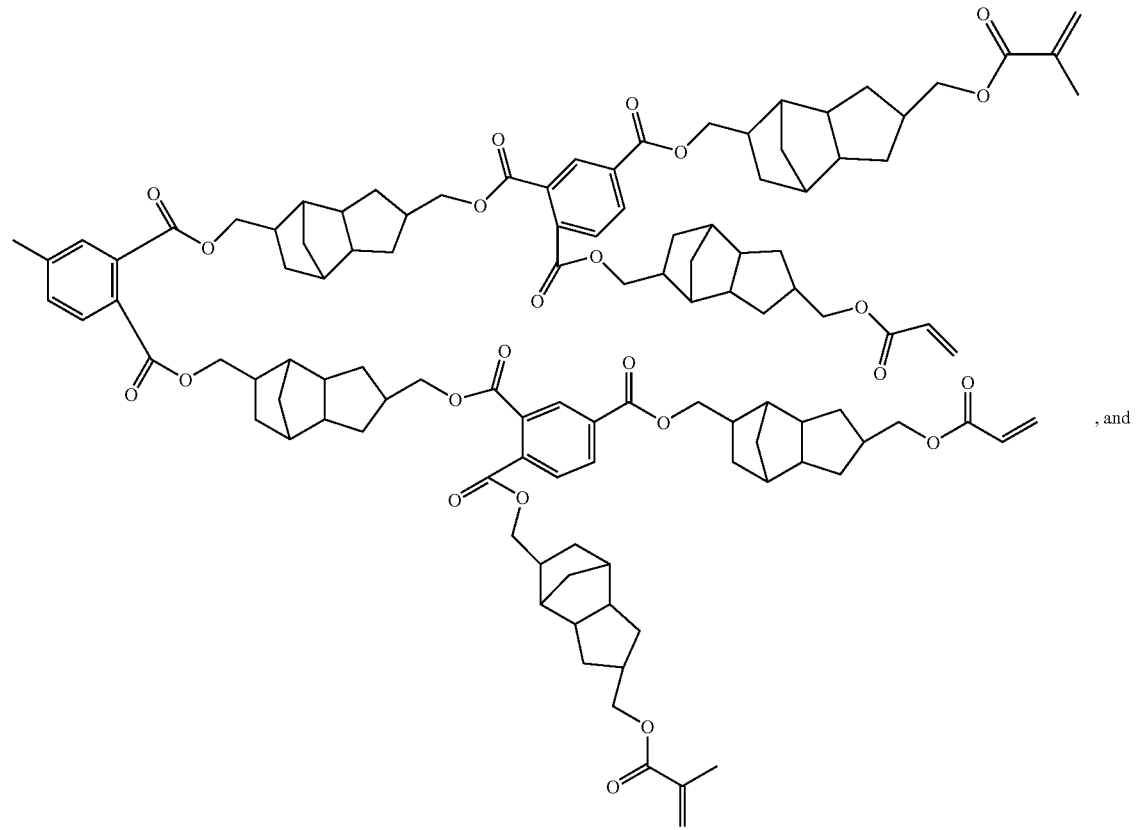
, and
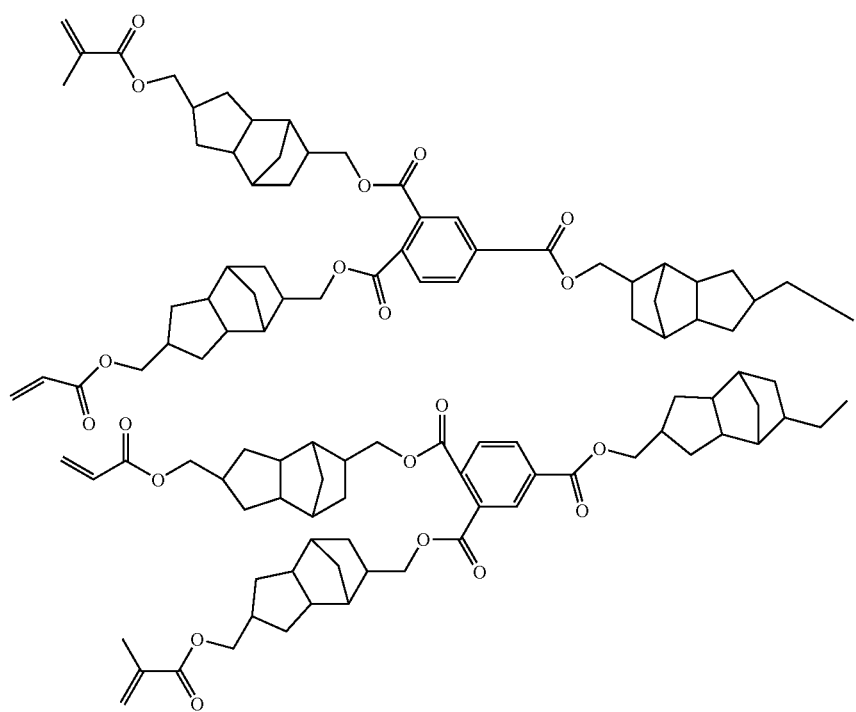

-continued

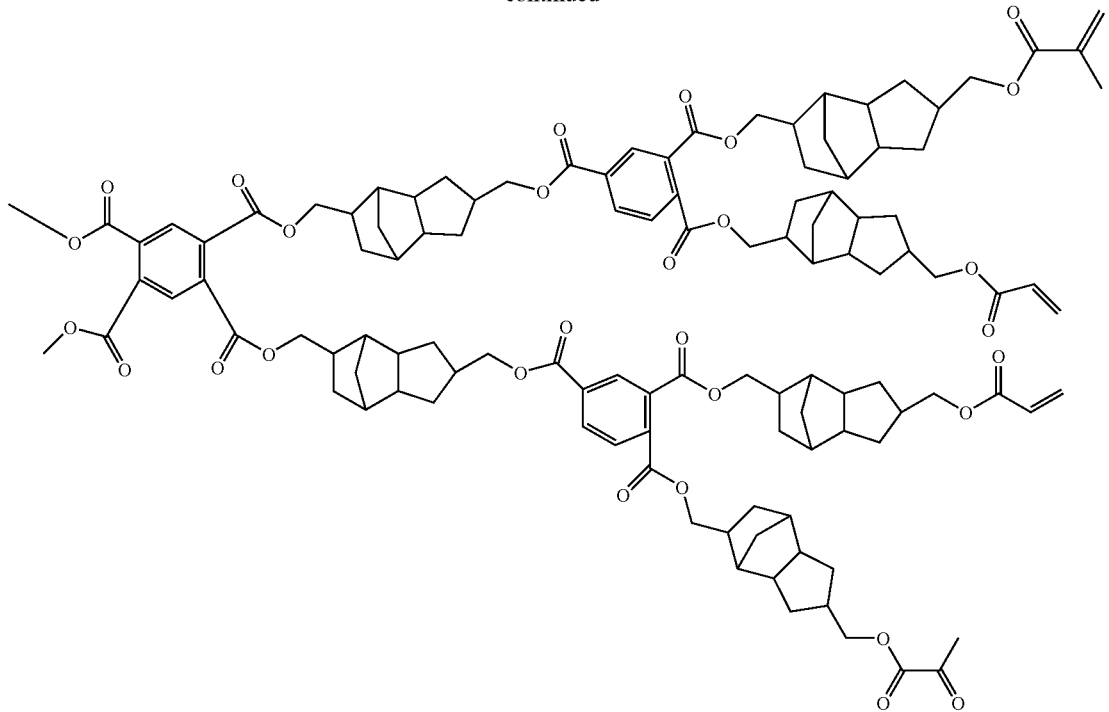

11. A compound having the structure:

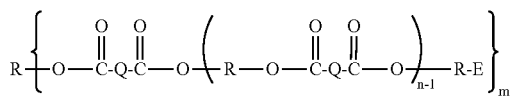

wherein:
each of R and Q is independently selected from the group consisting of substituted or unsubstituted aliphatic, aryl and heteroaryl moieties;
m is an integer having the value of 3 or 4; and
n is integer having the value of between 1 and about 10; and
each E is independently selected from the group consisting of an maleimide, styrenic, vinyl ester, an olefin, allyl, vinyl ether, itaconate, fumarate, oxetane, oxazoline, benzoxazine, cyanate ester and propargyl ether.

12. The compound of claim 11, wherein R is a substituted or an unsubstituted cycloalkyl having between 5 and about 20 carbon atoms.

13. The compound of claim 11, wherein R is a substituted or an unsubstituted cycloalkyl having between 5 and about 12 carbon atoms.

14. The compound of claim 11, wherein R is selected from the group consisting of a substituted cyclopentyl, an unsubstituted cyclopentyl, cyclohexyl, norbornyl, tricyclododecyl and dicyclopentadienyl.

15. The compound of claim 11, wherein Q is a substituted or an unsubstituted aryl or heteroaryl having between 6 and about 14 carbon atoms.

16. The compound of claim 11, wherein Q is selected from the group consisting of a substituted or an unsubstituted phenyl and a substituted or an unsubstituted naphthyl.

17. The compound of claim 11, wherein Q is a substituted or an unsubstituted cycloalkyl.

18. The compound of claim 11, wherein Q is a substituted or an unsubstituted norbornenyl.

19. The compound of claim 11, wherein substituted aliphatic, aryl, or heteroaryl moieties comprise substituents selected from the group consisting of an alkyl, an alkenyl, an alkynyl, hydroxy, oxo, an alkoxy, mercapto, a cycloalkyl, a substituted cycloalkyl, a heterocyclic, a substituted heterocyclic, an aryl, a substituted aryl, a heteroaryl, a substituted heteroaryl, an aryloxy, a substituted aryloxy, a halogen, a haloalkyl, cyano, nitro, nitrone, an amino, an amido, —C(O)H, —C(O)—O—, —C(O)—, —S—, —S(O)$_2$—, —OC(O)—O—, —NR—C(O)—, —NR—C(O)—NR— and —OC(O)—NR—, wherein R is selected from the group consisting of H, a lower alkyl, an acyl, an oxyacyl, carboxyl, carbamate, sulfonyl, a sulfonamide and sulfuryl.

* * * * *